(12) United States Patent
Vandenburgh

(10) Patent No.: US 6,503,504 B1
(45) Date of Patent: *Jan. 7, 2003

(54) DELIVERY OF BIOACTIVE COMPOUNDS TO AN ORGANISM

(75) Inventor: Herman H. Vandenburgh, Providence, RI (US)

(73) Assignee: Miriam Hospital, Providence, RI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/896,152

(22) Filed: Jul. 17, 1997

Related U.S. Application Data

(63) Continuation-in-part of application No. 08/712,111, filed on Sep. 13, 1996, now Pat. No. 5,869,041, which is a continuation-in-part of application No. 08/587,376, filed on Jan. 12, 1996, now abandoned.

(51) Int. Cl.$^7$ .......................... A61K 48/00; C12N 5/00; A61F 2/36
(52) U.S. Cl. ..................... 424/93.21; 435/325; 435/366; 435/373; 435/391; 623/23.72; 623/915
(58) Field of Search .............................. 424/93.2, 93.21; 435/29, 325, 455, 366, 373, 391; 623/23.72, 915

(56) References Cited

U.S. PATENT DOCUMENTS

| | | | |
|---|---|---|---|
| 5,266,480 A | * 11/1993 | Naughton et al. | 435/371 |
| 5,538,722 A | 7/1996 | Blau et al. | |
| 5,541,107 A | * 7/1996 | Naughton et al. | 435/29 |
| 5,869,041 A | * 2/1999 | Vandenburgh et al. | 424/93.21 |

FOREIGN PATENT DOCUMENTS

| | | |
|---|---|---|
| WO | WO93/00439 | 1/1993 |
| WO | WO93/21859 | 11/1993 |

OTHER PUBLICATIONS

Orkin and Motulsky (Dec. 7, 1995) NIH Report and Recommendations of the Panel to Assess the NIH Investment in the Research on Gene Therapy.*
Mulligen (1993) Science 260, 926–932.*
Dhawan et al. (1991) Science 254, 1509–1512.*
Vandenburgh et al. (1991) FASEB J. 5, 2860–2867.*
Perrone, Fenwick–Smith and Vandenburgh, 1994, Collagen and Stretch Modulate Autocrine Secretion of Insulin–like Growth Factor–1 and Insulin–like Growth Factor Binding Proteins from Differentiated Skeletel Muscle Cells, *The Journal of Biological Chemistry*.

* cited by examiner

Primary Examiner—Deborah Crouch
(74) *Attorney, Agent, or Firm*—Kathleen Madden Williams; Elizabeth N. Spar; Palmer & Dodge LLP

(57) ABSTRACT

Disclosed herein is a method of delivering a bioactive compound to an organism that involves growing individual cells in vitro under conditions that allow the formation of an organized tissue, at least a subset of the cells containing a foreign DNA sequence which mediates the production of the bioactive compound; and implanting the organized tissue into the organism, whereby the bioactive compound is produced and delivered to the organism. Also disclosed herein is an in vitro method for producing a tissue having in vivo-like gross and cellular morphology that involves providing precursor cells of the tissue; mixing the cells with a solution of extracellular matrix components to create a suspension; placing the suspension in a vessel having a three dimensional geometry approximating the in vivo gross and cellular morphology of the tissue and having attachment surfaces coupled thereto; allowing the suspension to coalesce; and culturing the cells under conditions in which the cells form an organized tissue connected to the attachment surfaces. Also disclosed herein is an apparatus for producing in vitro a tissue having in vivo-like gross and cellular morphology. This apparatus includes a vessel having a three dimensional geometry approximating the in vivo morphology of the tissue and tissue attachment surfaces coupled thereto.

15 Claims, 17 Drawing Sheets

FIG. 5
FIG. 6A
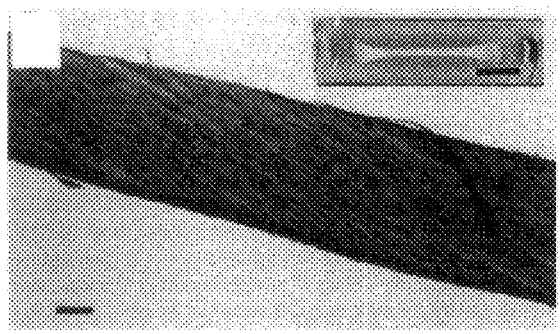
FIG. 6B
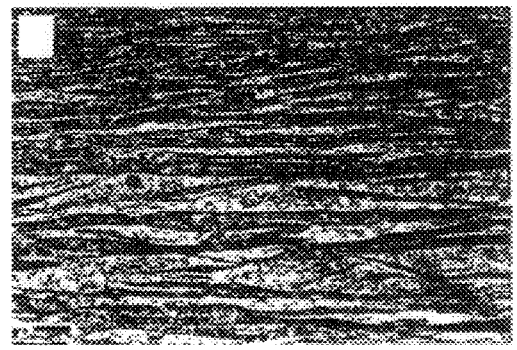
Recombinant Retroviruses
Expressing Growth Hormone
or Insulin-like Growth Factor-1
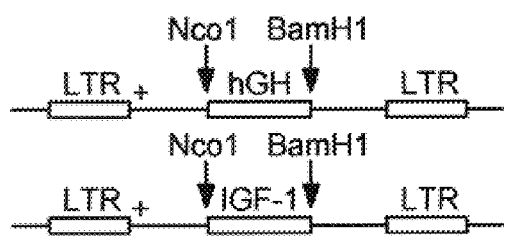
FIG. 6C
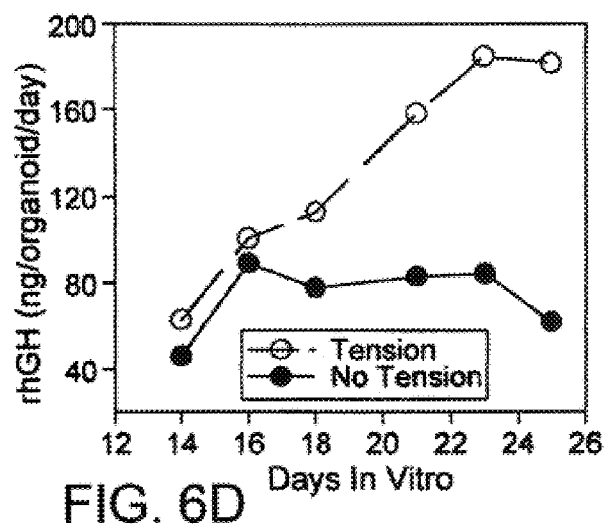
FIG. 6D

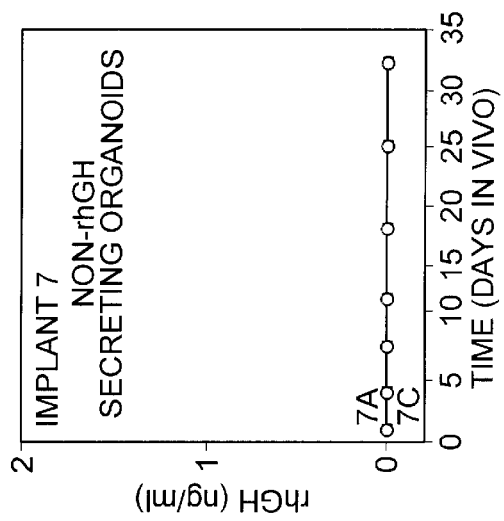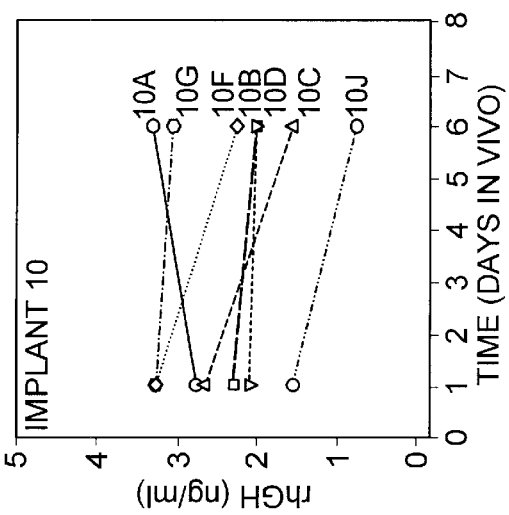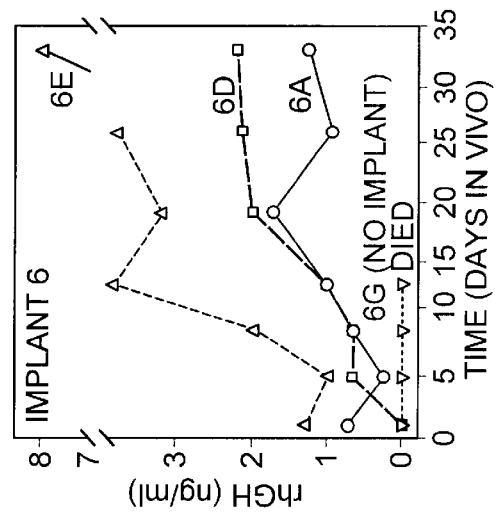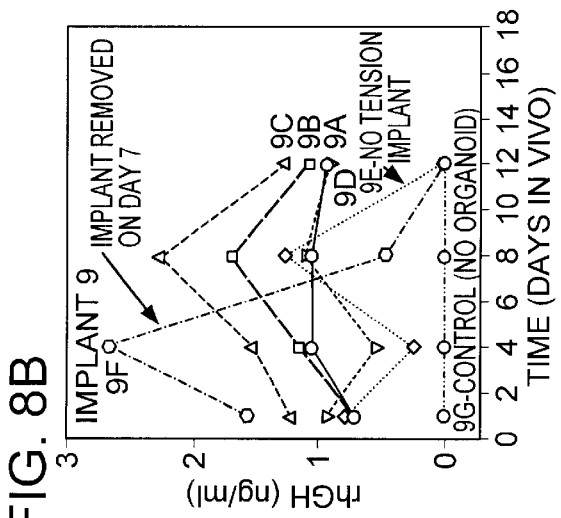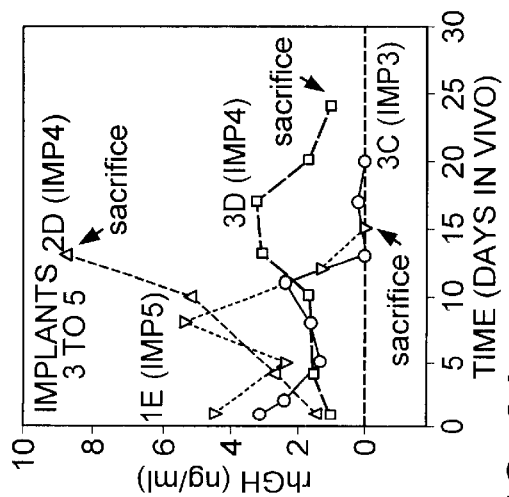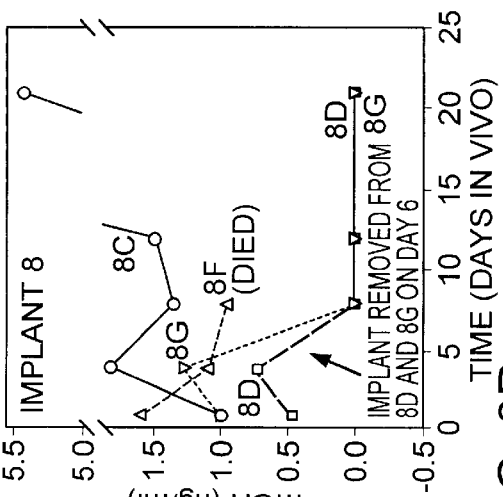
FIG. 8A  FIG. 8B  FIG. 8C
FIG. 8D  FIG. 8E  FIG. 8F Mouse Urinary Protein (MUP)

MW 20,000 D

DELIVERY OF BIOACTIVE COMPOUNDS TO AN ORGANISM

This application is a continuation-in-part of U.S. Ser. No. 08/712,111, filed Sep. 13, 1996, now U.S. Pat. No. 5,869,041, which is a continuation-in-part of U.S. Ser. No. 08/587,376, filed Jan. 12, 1996, now abandoned.

BACKGROUND OF THE INVENTION

This invention relates to the delivery of bioactive compounds to an organism, and in particular to methods and apparatus for the delivery of bioactive compounds by implanting into the organism an organized tissue producing the compounds.

One of the primary therapies used to treat disease is the delivery of bioactive compounds to the affected organism. Bioactive compounds may be delivered systemically or locally by a wide variety of methods. For example, an exogenous source (i.e., produced outside the organism treated) of the bioactive compound may be provided intermittently by repeated doses. The route of administration may include oral consumption, injection, or tissue absorption via topical compositions, suppositories, inhalants, or the like. Exogenous sources of the bioactive compound may also be provided continuously over a defined time period. For example, delivery systems such as pumps, time-released compositions, or the like may be implanted into the organism on a semi-permanent basis for the administration of bioactive compounds (e.g., insulin, estrogen, progesterone, etc.).

The delivery of bioactive compounds from an endogenous source (i.e., produced within the organism treated) has also been attempted. Traditionally, this was accomplished by transplanting, from another organism, an organ or tissue whose normal physiological function was the production of the bioactive compound (e.g., liver transplantation, kidney transplantation, or the like). More recently, endogenous production by cells of the affected organism has been accomplished by inserting into the cells a DNA sequence which mediates the production of the bioactive compound. Commonly known as gene therapy, this method includes inserting the DNA sequence into the cells of the organism in vivo. The DNA sequence persists either transiently or permanently as an extra-chromosomal vector (e.g., when inserted by adenovirus infection or by direct injection of a plasmid) or integrates into the host cell genome (e.g., when inserted by retrovirus infection). Alternatively, the DNA sequence may be inserted into cells of the host tissue or an another organism in vitro, and the cells subsequently transplanted into the organism to be treated.

SUMMARY OF THE INVENTION

In general, the invention features a method of delivering a bioactive compound to an organism. The method includes the steps of growing a plurality of cells in vitro under conditions that allow the formation of an organized tissue, at least a subset of the cells containing a foreign DNA sequence which mediates the production of the bioactive compound, and implanting the cells into the organism, whereby the bioactive compound is produced and delivered to the organism.

In a preferred embodiment of this method, the step of growing may include mixing the cells with a solution of extracellular matrix components to create a suspension, placing the suspension in a vessel having a three-dimensional geometry approximating the in vivo gross morphology of the tissue and having tissue attachments surfaces thereon, allowing the suspension to coalesce, and culturing the coalesced suspension under conditions in which the cells connect to the attachment surfaces and form a tissue having an in vivo-like gross and cellular morphology.

In other preferred embodiments, the DNA sequence encodes the bioactive compound; the DNA sequence encodes a protein which mediates the production of the bioactive compound (for example, by regulating its expression or encoding an intermediate to the bioactive compound); the DNA sequence mediates the production of two bioactive compounds; the tissue includes skeletal muscle; the tissue includes myotubes; the bioactive compound is a growth factor (for example, human growth hormone); the bioactive compound is a bone morphogenetic protein; the bone morphogenetic protein is BMP-6; the organized tissue is implanted into the tissue of origin of at least one of the cells; the cells include a first and a second population of cells, at least a subset of each of the populations containing a foreign DNA sequence which mediates the production of a bioactive compound; the foreign DNA sequence of the first population mediates the production of a bioactive compound different from the foreign DNA sequence of the second population; and the foreign DNA sequence of the first population encodes a bone morphogenetic protein and the foreign DNA sequence of the second population includes a parathyroid hormone.

In other preferred embodiments, the method includes: the step of removing the organized tissue from the organism to terminate delivery of the bioactive compound; following the removal step, the step of culturing the organized tissue in vitro under conditions which preserve its in vivo viability; following the culturing step, the step of reimplanting the organized tissue into the organism to deliver the bioactive compound to the organism; the step of isolating primary cell types of at least one of the cell types of the tissue; and the step of utilizing immortalized cells of at least one of the cell types of the tissue.

In other preferred embodiments of this method, the tissue comprises substantially post-mitotic cells; during the growing step, a force is exerted substantially parallel to a dimension of the tissue; the force is exerted on the individual cells during growth in vitro and on the organized tissue during implantation in vivo; the coalesced suspension exerts a force on the cells substantially parallel to a dimension of the vessel; the cells are aligned substantially parallel to a dimension of the vessel; the vessel is substantially semi-cylindrical in shape; the attachment surfaces are positioned at opposite ends of the vessel; the alignment is mediated by forces exerted by the coalesced suspension; the cells comprise myotubes; the organism is a mammal; and the mammal is a human.

In a related aspect, the invention features an organized tissue producing a bioactive compound, the tissue is produced by the steps of mixing a plurality of cells with a solution of extracellular matrix components to create a suspension, at least a subset of the cells containing a foreign DNA sequence which mediates the production of a bioactive compound; placing the suspension in a vessel having a three dimensional geometry approximating the in vivo gross morphology of the tissue, the vessel having attachment surfaces thereon; allowing the suspension to coalesce; and culturing the coalesced suspension under conditions in which the cells connect to the attachment surfaces and form a tissue having an in vivo-like gross and cellular morphology.

In a related aspect, the invention features an organized tissue producing a bioactive compound. The organized tissue includes a plurality of cells, grown in vitro under conditions that allow the formation of an organized tissue, and a foreign DNA sequence mediating the production of a bioactive compound. The DNA sequence is inserted into at least a subset of the cells. Also included in the invention are organized tissues producing a bioactive compound, the tissue being produced by any of the methods described herein.

In preferred embodiments, the organized tissue is skeletal muscle.

In a related aspect, the invention features an in vitro method for producing a tissue having an in vivo-like gross and cellular morphology. The method includes providing precursor cells of the tissue; mixing the cells with a solution of extracellular matrix components to create a suspension; placing the suspension in a vessel having a three-dimensional geometry approximating the in vivo gross morphology of the tissue, the vessel having tissue attachment surfaces thereon; allowing the suspension to coalesce; and culturing the cells under conditions in which the cells form an organized tissue connected to the attachment surfaces.

In preferred embodiments of this method, the step of providing includes isolating primary cells of at least one of the cell types which make up the tissue or includes utilizing immortalized cells of at least one of the cell types which make up the tissue; the step of providing includes inserting a foreign DNA sequence into at least one of the cells which make up the tissue; the tissue includes substantially post-mitotic cells; the coalesced suspension exerts a force on the cells substantially parallel to a dimension of the vessel; the cells are aligned substantially parallel to a dimension of the vessel; the vessel is substantially semi-cylindrical in shape; and the attachment surfaces are positioned at opposite ends of the vessel.

In other preferred embodiments of this method, the DNA sequence encodes the bioactive compound; the DNA sequence encodes a protein which mediates the production of the bioactive compound; the DNA sequence mediates the production of two bioactive compounds; the bioactive compound is a growth factor; the organized tissue is implanted into the organism, whereby the bioactive compound is produced and delivered to the organism; and the organized tissue is implanted into the tissue of origin of at least one of the cells.

In a related aspect, the invention features an organized tissue produced by the steps of providing precursor cells of the tissue; mixing the cells with a solution of extracellular matrix components to create a suspension; placing the suspension in a vessel having a three-dimensional geometry approximating the in vivo gross morphology of the tissue, the vessel having tissue attachment surfaces thereon; allowing the suspension to coalesce; and culturing the cells under conditions in which the cells form an organized tissue connected to the attachment surfaces. Also included in the invention are organized tissues produced by any of the methods described herein.

In a related aspect, the invention features an apparatus for producing a tissue in vitro having an in vivo-like gross and cellular morphology. The apparatus includes a vessel having a three-dimensional geometry approximating the in vivo gross morphology of the tissue and having tissue attachment surfaces in the vessel.

In preferred embodiments of this aspect of the invention, the apparatus further includes a culture chamber in which the vessel may be submerged; the vessel is substantially semi-cylindrical in shape; the attachment surfaces are coupled to opposite ends of the semi-cylindrical vessel; the coalesced suspension exerts a force on the cells substantially parallel to a dimension of the vessel; and the cells are aligned substantially parallel to a dimension of the vessel.

In a related aspect, the invention features a method of regulating bone formation in an organism. The method includes the steps of growing a plurality of cells in vitro under conditions that allow the formation of an organized tissue, at least a subset of the cells containing a foreign DNA sequence which mediates the production of a bone morphogenetic protein, and implanting the tissue into the organism, whereby the bone morphogenetic protein is produced and delivered to chondroblastic or osteoblastic precursor cells.

In a preferred embodiment of this method, the step of growing may include mixing the cells with a solution of extracellular matrix components to create a suspension; placing the suspension in a vessel having a three-dimensional geometry approximating the in vivo gross morphology of the tissue and having tissue attachments surfaces thereon; allowing the suspension to coalesce; and culturing the coalesced suspension under conditions in which the cells connect to the attachment surfaces and form a tissue having an in vivo-like gross and cellular morphology.

In other preferred embodiments, the DNA sequence encodes the bone morphogenetic protein; the DNA sequence encodes BMP-6; the DNA sequence encodes a protein which mediates the production of the bone morphogenetic protein (for example, by regulating its expression or encoding an intermediate to the bioactive compound); the DNA sequence also mediates the production of another bioactive compound; the tissue includes skeletal muscle; the tissue includes myotubes; the bioactive compound is a growth factor (for example, human growth hormone); the organized tissue is implanted into the tissue of origin of at least one of the cells; the cells include a first and a second population of cells, at least a subset of each of the populations containing a foreign DNA sequence which mediates the production of a bioactive compound; the foreign DNA sequence of the first population mediates the production of a bioactive compound different from the foreign DNA sequence of the second population; and the foreign DNA sequence of the first population encodes a bone morphogenetic protein and the foreign DNA sequence of the second population includes a parathyroid hormone.

In other preferred embodiments, the method includes: the step of removing the organized tissue from the organism to terminate delivery of the bone morphogenetic protein; following the removal step, the step of culturing the organized tissue in vitro under conditions which preserve its in vivo viability; following the culturing step, the step of reimplanting the organized tissue into the organism to deliver the bone morphogenetic protein to the organism; the step of isolating primary cell types of at least one of the cell types of the tissue; and the step of utilizing immortalized cells of at least one of the cell types of the tissue.

In other preferred embodiments of this method, the tissue comprises substantially post-mitotic cells; during the growing step, a force is exerted substantially parallel to a dimension of the tissue; the force is exerted on the individual cells during growth in vitro and on the organized tissue during implantation in vivo; the coalesced suspension exerts a force on the cells substantially parallel to a dimension of the vessel; the cells are aligned substantially parallel to a dimension of the vessel; the vessel is substantially semi-cylindrical in shape; the attachment surfaces are positioned at opposite ends of the vessel; the alignment is mediated by forces exerted by the coalesced suspension; the cells comprise myotubes; the organism is a mammal; and the mammal is a human.

As used herein, by a "bioactive compound" is meant a compound which influences the biological structure, function, or activity of a cell or tissue of a living organism.

By "bone morphogenetic protein" is meant an extracellular osteogenic-stimulating molecule belonging to the TGF-β superfamily. Bone morphogenetic proteins ("BMP") include a large number of proteins, for example, BMP-2, -3, -4, -5, -6, -7, -11, and -12. Bone morphogenetic proteins control the cellular events associated with bone and cartilage formation and repair (e.g., cellular growth, proliferation, and differentiation). For example, bone morphogenetic proteins alter the differentiation pathway of mesenchymal cells towards the chondroblastic or osteoblastic lineage.

By "organized tissue" or "organoid" is meant a tissue formed in vitro from a collection of cells having a cellular organization and gross morphology similar to that of the tissue of origin for at least a subset of the cells in the collection. An organized tissue or organoid may include a mixture of different cells, for example, muscle (including but not limited to striated muscle, which includes both skeletal and cardiac muscle tissue), fibroblast, and nerve cells, but must exhibit the in vivo cellular organization and gross morphology that is characteristic of a given tissue including at least one of those cells, for example, the organization and morphology of muscle tissue may include parallel arrays of striated muscle tissue.

By "in vivo-like gross and cellular morphology" is meant a three-dimensional shape and cellular organization substantially similar to that of the tissue in vivo.

By "extracellular matrix components" is meant compounds, whether natural or synthetic compounds, which function as substrates for cell attachment and growth. Examples of extracellular matrix components include, without limitation, collagen, laminin, fibronectin, vitronectin, elastin, glycosaminoglycans, proteoglycans, and combinations of some or all of these components (e.g., Matrigel™, Collaborative Research, Catalog No. 40234).

By "tissue attachment surfaces" is meant surfaces having a texture, charge or coating to which cells may adhere in vitro. Examples of attachment surfaces include, without limitation, stainless steel wire, VELCRO™, suturing material, native tendon, covalently modified plastics (e.g., RGD complex), and silicon rubber tubing having a textured surface.

By "foreign DNA sequence" is meant a DNA sequence which differs from that of the wild type genomic DNA of the organism and may be extra-chromosomal, integrated into the chromosome, or the result of a mutation in the genomic DNA sequence.

By "substantially post-mitotic cells" is meant an organoid in which at least 50% of the cells containing a foreign DNA sequence are non-proliferative. Preferably, organoids including substantially post-mitotic cells are those in which at least 80% of the cells containing a foreign DNA sequence are non-proliferative. More preferably, organoids including substantially post-mitotic cells are those in which at least 90% of the cells containing a foreign DNA sequence are non-proliferative. Most preferably, organoids including substantially post-mitotic cells are those in which 99% of the cells containing a foreign DNA sequence are non-proliferative. Cells of an organoid retaining proliferative capacity may include cells of any of the types included in the tissue. For example, in striated muscle organoids such as skeletal muscle organoids, the proliferative cells may include muscle stem cells (i.e., satellite cells) and fibroblasts.

The invention provides a number of advantages. For example, implantation of an organized tissue produced in vitro provides quantifiable, reproducible, and localized delivery of bioactive compounds to an organism. Prior to implantation, the production of bioactive compounds by the organized tissue may be measured and quantified per unit time, per unit mass, or relative to any other physiologically-relevant parameter. In addition, the capability of an organized tissue to sustain production of bioactive compounds can be assessed by culturing for extended periods and assaying of compound production with time.

Moreover, because the organized tissue is implanted at a defined anatomical location as a discrete collection of cells, it may be distinguished from host tissues, removed post-implantation from the organism, and reimplanted into the organism at the same or a different location at the time of removal or following an interim period of culturing in vitro. This feature facilitates transient or localized delivery of the bioactive compound. Restriction of the cells producing bioactive compounds to particular anatomical sites also enhances the controlled delivery of bioactive compounds, especially where the organized tissue functions as a paracrine organ. The efficiency of delivery of a bioactive compound (i.e., the amount of the bioactive compound delivered to obtain a desired serum concentration) is also enhanced as compared to direct subcutaneous injection. Likewise, the efficiency of implanting post-mitotic cells containing a foreign DNA sequence into an organism (i.e., the number of cells in a post-mitotic state as a percentage of the initial number of cells containing the foreign DNA sequence) is enhanced by organoid implantation as compared to the implantation of individual mitotic cells. For example, skeletal muscle organoids produced in vitro include post-mitotic myofibers representing greater than 70% of the initial myoblasts containing a foreign DNA sequence, whereas direct implantation of the myoblasts results in post-mitotic myofibers representing less than 1% of the initial cells.

In addition, because substantially all of the implanted cells are fully differentiated, migration of these cells to other anatomical sites is reduced. Moreover, implantation of post-mitotic, non-migratory myofibers containing a foreign DNA reduces the possibility of cell transformation and tumor formation. The implantation of an organized tissue may even enhance the functional and structural characteristics of the host tissue.

Furthermore, because the method of producing a tissue having an in vivo-like gross and cellular morphology may be achieved without the application of external forces by mechanical devices, the apparatus for producing such a tissue is readily adaptable to standard cell and tissue culture systems. The apparatus and method may also be used to produce bone, cartilage, tendon, and cardiac tissues as these tissues include cell types which organize in response to external forces. In addition, the apparatus includes widely available, easily assembled and relatively inexpensive components.

Other advantages and features of the invention will be apparent from the detailed description, and from the claims.

BRIEF DESCRIPTION OF THE DRAWINGS

FIG. 5 is a micrograph of a section of a skeletal muscle organoid grown in vitro from rhGH-secreting C2C12 cells which has been stained for sarcomeric tropomyosin.

FIG. 6(A) illustrates bioartificial organoids engineered from C2C12 myoblasts (C2-organoid) and stained with an antibody to sarcomeric tropomyosin to show the organized muscle fibers. Inset in (A) shows an unstained organoid approximately 30 mm in length; bar equals 0.25 mm and 0.05 mm in inset.

FIG. 6(B) illustrates organoids engineered from primary neonatal rat myoblasts (R-organoid) and stained with an antibody to sarcomeric tropomyosin to show the organized muscle fibers.

FIG. 6(C) is a schematic illustration of retroviral expression constructs which have been used to transduce primary Fisher 344 myoblasts and engineered into R-organoids expressing physiological levels of rhGH.

FIG. 6(D) is a graph showing physiological levels of rhGH produced by R-organoids transduced with the rhGH construct shown in FIG. 6(C).

FIGS. 8A–8F are graphs of rhGH serum levels in mice following skeletal muscle organoid implantation.

DETAILED DESCRIPTION

Figure 1:
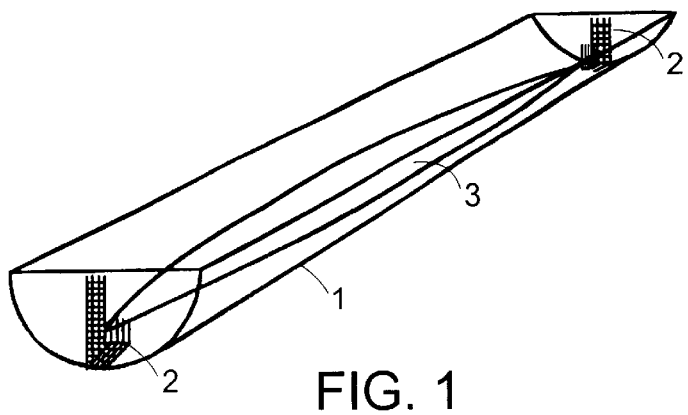
FIG. 1 is a diagram of a vessel for growing skeletal muscle tissue which will have an in vivo-like gross and cellular morphology.

I. In Vitro Production of Tissues Having In Vivo-like Gross and Cellular Morphology Organized tissues having in vivo-like gross and cellular morphology may be produced in vitro from the individual cells of a tissue of interest. As a first step in this process, disaggregated or partially disaggregated cells are mixed with a solution of extracellular matrix components to create a suspension. This suspension is then placed in a vessel having a three dimensional geometry which approximates the in vivo gross morphology of the tissue and includes tissue attachment surfaces coupled to the vessel. The cells and extracellular matrix components are then allowed to coalesce or gel within the vessel, and the vessel is placed within a culture chamber and surrounded with media under conditions in which the cells are allowed to form an organized tissue connected to the attachment surfaces.

Although this method is compatible with the in vitro production of a wide variety of tissues, it is particularly suitable for tissues in which at least a subset of the individual cells are exposed to and impacted by mechanical forces during tissue development, remodeling or normal physiologic function. Examples of such tissues include muscle, bone, skin, nerve, tendon, cartilage, connective tissue, endothelial tissue, epithelial tissue, and lung. More specific examples include skeletal and cardiac (i.e., striated), and smooth muscle, stratified or lamellar bone, and hyaline cartilage. Where the tissue includes a plurality of cell types, the different types of cells may be obtained from the same or different organisms, the same or different donors, and the same or different tissues. Moreover, the cells may be primary cells or immortalized cells. Furthermore, all or some of the cells of the tissue may contain a foreign DNA sequence which mediates the production of a bioactive compound (as described herein).

The composition of the solution of extracellular matrix components will vary according to the tissue produced. Representative extracellular matrix components include, but are not limited to, collagen, laminin, fibronectin, vitronectin, elastin, glycosaminoglycans, proteoglycans, and combinations of some or all of these components (e.g., Matrigel™, Collaborative Research, Catalog No. 40234). In tissues containing cell types which are responsive to mechanical forces, the solution of extracellular matrix components preferably gels or coalesces such that the cells are exposed to forces associated with the internal tension in the gel.

Culture conditions will also vary according to the tissue produced. Methods for culturing cells are well known in the art and are described, for example, in *Skeletal Cell Culture: A Practical Approach*, (R. I. Fveshney, ed. IRL Press, 1986). In general, the vessel containing a coalesced suspension of cells and extracellular matrix components is placed in a standard culture chamber (e.g., wells, dishes, or the like), and the chamber is then filled with culture medium until the vessel is submerged. The composition of the culture medium is varied, for example, according to the tissue produced, the necessity of controlling the proliferation or differentiation of some or all of the cells in the tissue, the length of the culture period and the requirement for particular constituents to mediate the production of a particular bioactive compound. The culture vessel may be constructed from a variety of materials in a variety of shapes as described below.

An apparatus for producing a tissue in vitro having an in vivo-like gross and cellular morphology includes a vessel having a three dimensional geometry which approximates the in vivo gross morphology of the tissue. The apparatus also includes tissue attachment surfaces coupled to the vessel. Such a vessel may be constructed from a variety of materials which are compatible with the culturing of cells and tissues (e.g., capable of being sterilized and compatible with a particular solution of extracellular matrix components) and which are formable into three dimensional shapes approximating the in vivo gross morphology of a tissue of interest. The tissue attachment surfaces (e.g., stainless steel mesh, VELCRO™, or the like) are coupled to the vessel and positioned such that as the tissue forms in vitro the cells may adhere to and align between the attachment surfaces. The tissue attachment surfaces may be constructed from a variety of materials which are compatible with the culturing of cells and tissues (e.g., capable of being sterilized, or having an appropriate surface charge, texture, or coating for cell adherence).

The tissue attachment surfaces may be coupled in a variety of ways to an interior or exterior surface of the vessel. Alternatively, the tissue attachment surfaces may be coupled to the culture chamber such that they are positioned adjacent the vessel and accessible by the cells during tissue formation. In addition to serving as points of adherence, in certain tissue types (e.g., muscle), the attachment surfaces allow for the development of tension by the tissue between opposing attachment surfaces. Moreover, where it is desirable to maintain this tension in vivo, the tissue attachment surfaces may be implanted into an organism along with the tissue (see further discussion in Section II.).

One vessel according to the invention is shown in FIG. 1. This vessel 1, which is suitable for the in vitro production of a skeletal muscle organoid 3, has a substantially semi-cylindrical shape and tissue attachment surfaces 2 coupled to an interior surface of the vessel.

Figure 2:
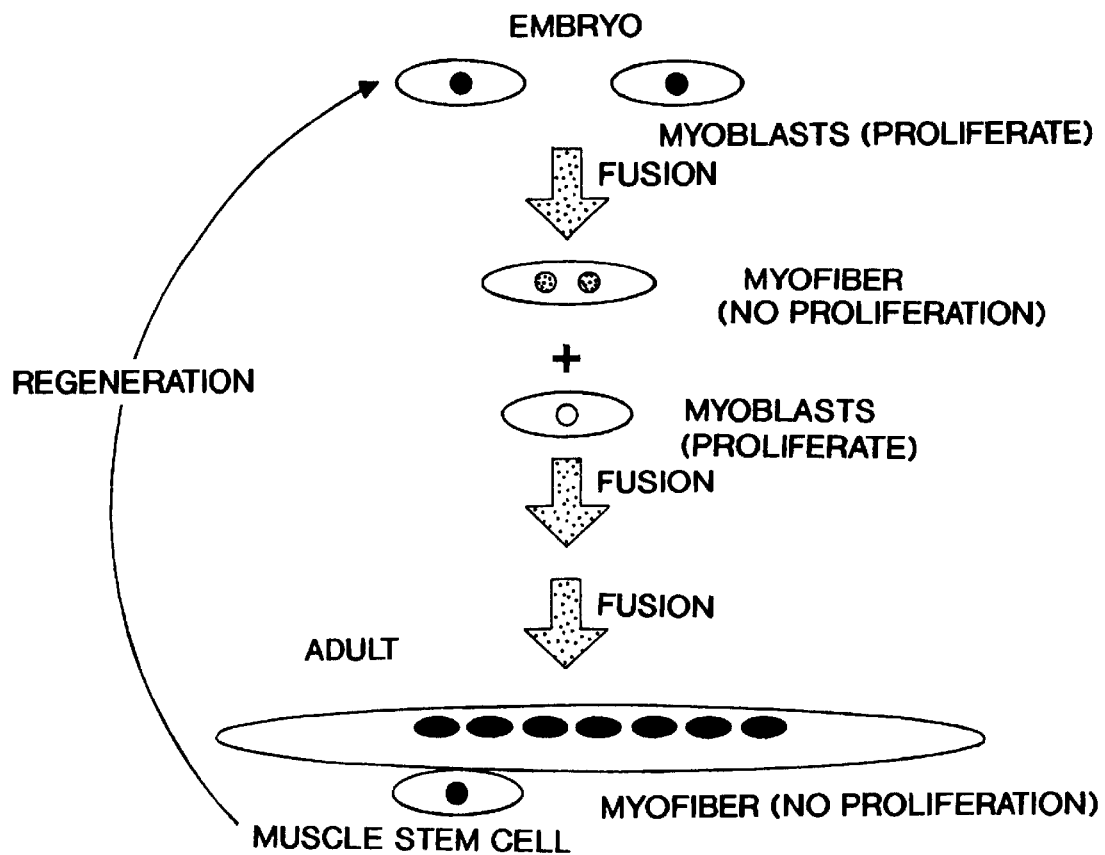
FIG. 2 is a flow chart of the process of skeletal muscle growth and regeneration.

A. In Vitro Production of a Skeletal Muscle Organoid Having In Vivo-Like Gross and Cellular Morphology Using an apparatus and method as generally described above, a skeletal muscle organoid having an in vivo-like gross and cellular morphology was produced in vitro. An overview of the stages of skeletal muscle growth and regeneration is shown in FIG. 2. As shown, during skeletal muscle development embryonic myoblasts proliferate, differentiate, and then fuse to form multi-nucleated myofibers. Although the myofibers are non-proliferative, a population of muscle stem cells (i.e., satellite cells), derived from the embryonic myoblast precursor cells, retain their proliferative capacity and serve as a source of myoblasts for muscle regeneration in the adult organism. Therefore, either embryonic myoblasts or adult skeletal muscle stem cells may serve as one of the types of precursor cells for in vitro production of a skeletal muscle organoid.

To produce skeletal muscle cells capable of secreting a bioactive compound, primary rat or avian cells or immortalized murine cells secreting recombinant human growth hormone, were suspended in a solution of collagen and Matrigel™ which was maintained at 4° C. to prevent gelling. The cell suspension was then placed in a semi-cylindrical vessel with tissue attachment surfaces coupled to an interior surface at each end of the vessel. The vessel was positioned in the bottom of a standard cell culture chamber. Following two to four hours of incubation at 37° C., the gelled cell suspension was covered with fresh culture medium (renewed at 24 to 72 hour intervals) and the chamber containing the suspended cells was maintained in a humidified 5% $CO_2$ incubator at 37° C. throughout the experiment.

Between the second and sixth day of culture, the cells were found to be organized to the extent that they spontaneously detached from the vessel. At this stage, the cells were suspended in culture medium while coupled under tension between tissue attachment surfaces positioned at either end of the culture vessel. During the subsequent ten to fourteen days, the cells formed an organoid containing skeletal myofibers aligned parallel to each other in three dimensions. The alignment of the myofibers and the gross and cellular morphology of the organoid were similar to that of in vivo skeletal muscle.

To carry out the above method, an apparatus for organoid formation was constructed from silastic tubing and either VELCRO™ or metal screens as follows. A section of silastic tubing (approximately 5 mm I.D., 8 mm O.D., and 30 mm length) was split in half with a razor blade and sealed at each end with silicone rubber caulking. Strips of VELCRO™ (loop or hook side, 3 mm wide by 4 mm long) or L-shaped strips of stainless steel screen (3 mm wide by 4 mm long by 4 mm high) were then attached with silicone rubber caulking to the interior surface of the split tubing near the sealed ends. The apparatus was thoroughly rinsed with distilled/deionized water and subjected to gas sterilization.

Skeletal muscle organoids were produced in vitro from a C2C12 mouse skeletal muscle myoblast cell line stably co-transfected with recombinant human growth hormone-expressing and β-galactosidase-expressing (β-gal) constructs. Dhawan et al., 1991, *Science* 254:1509–1512. Cells were plated in the vessel at a density of $1-4 \times 10^6$ cells per vessel in 400 μl of a solution containing extracellular matrix components. The suspension of cells and extracellular matrix components was achieved by the following method. The solution includes 1 part Matrigel™ (Collaborative Research, Catalog No. 40234) and 6 parts of a 1.6 mg/ml solution of rat tail Type I collagen (Collaborative Research, Catalog No. 40236). The Matrigel™ was defrosted slowly on ice and kept chilled until use. The collagen solution was prepared just prior to cell plating by adding to lyophilized collagen, growth medium (see constituents below), and 0.1N NaOH in volumes equivalent to 90% and 10%, respectively, of the volume required to obtain a final concentration of 1.6 mg/ml and a pH of 7.0–7.3. The collagen, sodium hydroxide and growth medium were maintained on ice prior to and after mixing by inversion.

Freshly centrifuged cells were suspended in the collagen solution by trituration with a chilled sterile pipet. Matrigel™ was subsequently added with a chilled pipet and the suspension was once again mixed by trituration. The suspension of cells and extracellular matrix components was maintained on ice until it was plated in the vessel using chilled pipet tips. The solution was pipetted and spread along the length of the vessel, taking care to integrate the solution into the tissue attachment surfaces. The culture chamber containing the vessel was then placed in a standard cell culture incubator, taking care not to shake or disturb the suspension. The suspension was allowed to gel, and after 2 hours the culture chamber was filled with growth medium such that the vessel was submerged.

For a period of three days the cells were maintained on growth medium containing DMEM-high glucose (GIBCO-BRL), 5% fetal calf serum (Hyclone Laboratories), and 1% penicillin/streptomycin solution (final concentration 100 units/ml and 0.1 µg/ml, respectively). On the fourth day of culture, the cells were switched to fusion medium containing DMEM-high glucose, 2% horse serum (Hyclone Laboratories), and 100 units/ml penicillin for a period of 4 days. On the eighth day of culture, the cells were switched to maintenance medium containing DMEM-high glucose, 10% horse serum, 5% fetal calf serum, and 100 units/ml penicillin for the remainder of the experiment. Before the organoids were ready for implantation, some were cultured in maintenance media containing 1 µg/ml of cytosine arabinoside for the final four to eight days. Treatment with cytosine arabinoside eliminated proliferating cells and produced organoids including substantially post-mitotic cells.

Figure 3:
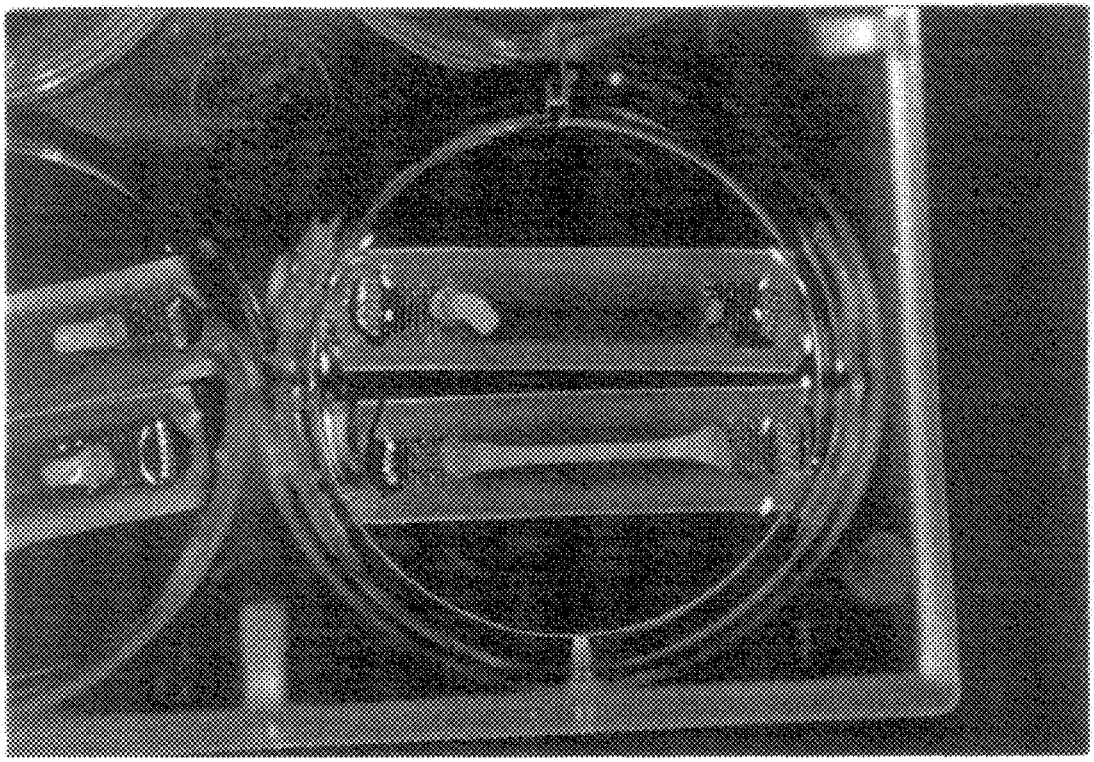
FIG. 3 is a photograph of skeletal muscle organoids formed in vitro from rhGH-secreting C2C12 cells 48 hours postplating. Top gel has detached and contracted.
Figure 4:
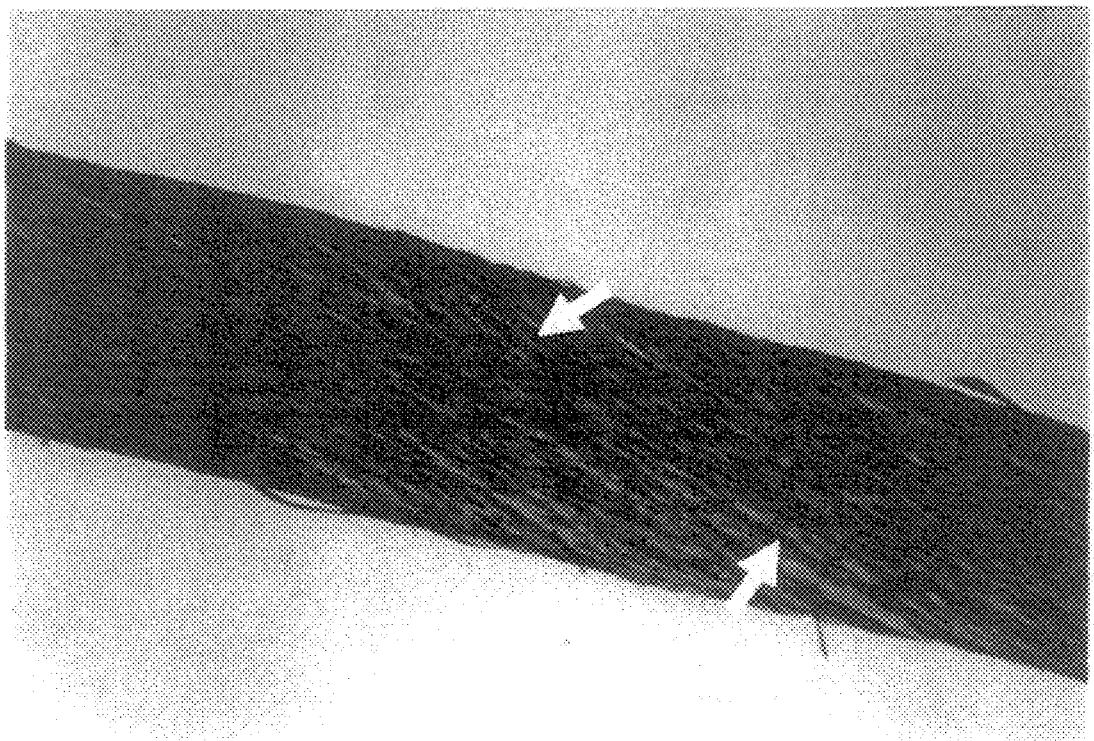
FIG. 4 is a micrograph of a section of a skeletal muscle organoid grown in vitro from rhGH-secreting C2C12 cells which has been stained for sarcomeric tropomyosin.

The cell-extracellular matrix gel (cell-gel) formed in vitro from these stably transfected C2C12 cells 48 hours after plating are shown in FIG. 3. In the upper half of the figure the cell-gel has detached from one of the tissue attachment surfaces. The resultant contraction demonstrates the tension developed in the gel between the tissue attachment surfaces. FIGS. 4 and 5 demonstrate the presence of a muscle-specific contractile protein (i.e., brown staining following incubation with an antibody to sarcomeric tropomyosin), in parallel arrays of highly organized and longitudinally oriented myofibers in mammalian skeletal muscle organoids following three weeks of culturing in the apparatus shown in FIG. 1. FIG. 4 represents a middle section of a 3 week old mammalian C2C12 muscle cell organoid stained for sarcomeric tropomyosin, showing longitudinally oriented myofibers (arrows). Magnification is approximately 40×. FIG. 5 shows parallel aligned myofibers (arrows) on the surface of a 3 week old mammalian C2C12 muscle cell organoid stained for sarcomeric tropomyosin. Magnification is approximately 400×. Moreover, FIG. 10B shows the retention of myofiber organization following organoid implantation.

II. Delivery of Bioactive Compounds

Bioactive compounds may be delivered to an organism by growing individual cells in vitro under conditions that result in the formation of an organized tissue producing the bioactive compound and subsequently implanting the organized tissue into the organism (see Section I. for detailed description of organized tissue production). Production of the bioactive compound by the organized tissue is mediated by a foreign DNA sequence present in at least a subset of the cells which make up the implanted tissue.

A variety of bioactive compounds may be delivered by this method, and they may function through intracellular (i.e., within the cells of the organized tissue or organoid), endocrine, autocrine, or paracrine mechanisms. Moreover, the organoid may deliver multiple bioactive compounds either simultaneously or sequentially (e.g., one bioactive compound mediates the delivery of another). Liberation of the bioactive compound from the cells of the organoid may occur by either passive or active processes (e.g., diffusion or secretion).

For example, the bioactive compound may be a hormone, growth factor, or the like which is produced and liberated by the cells of the organoid to act locally or systemically on host tissues. Alternatively, the bioactive compound may function within the cells or on the surface of the cells of the organoid to enhance the uptake or metabolism of compounds from the host tissue or circulation (e.g., lactic acid, low density lipoprotein). Where the organoid serves as a functional and structural adjunct to the host tissue, delivery of growth factors by autocrine or paracrine mechanisms may enhance the integration of the organoid into host tissues. Similarly, where multiple bioactive compounds are produced by the organoid, autocrine delivery of one of the bioactive compounds may be used to regulate the production of one or more of the other bioactive compounds.

The organoid may be implanted by standard laboratory or surgical techniques at a desired anatomical location within the organism. For example, the organoid may be implanted in the same or a different tissue from the tissue of origin of at least one of the individual cells. The location of implantation depends, in part, upon the method of delivery and the identity of the particular bioactive compound to be delivered. For example, an organoid acting as an endocrine organ may be implanted in or adjacent a highly vascularized host tissue. Alternatively, an organoid acting as a paracrine organ is preferably implanted in or adjacent to the host tissue to which the bioactive compound is to be delivered.

The organoid may be implanted by attachment to a host tissue or as a free floating tissue. In addition, attached organoids may be implanted with or without the tissue attachment surfaces used for in vitro tissue formation. Tissues responsive to mechanical forces are preferably implanted by attaching directly to the host tissue or by implanting the organoid coupled to the attachment surfaces so that the organoid is exposed to mechanical forces in vivo. For example, skeletal muscle organoids are preferably implanted by attachment to the host tissue under tension along a longitudinal axis of the organoid. Moreover, the organoids may be permanently or temporarily implanted. Permanent implantation may be preferred, for example, where the organoid produces a bioactive compound which corrects a systemic metabolic error (e.g., delivery of insulin to treat diabetes), whereas temporary implantation may be preferred where only transient delivery of a bioactive compound is desired (e.g., delivery of a growth factor to enhance wound healing). Furthermore, because organoids may be implanted, removed, and maintained in vitro (see FIG. 10A and discussion below), bioactive compounds may be delivered intermittently to the same or a different location in the organism. For example, a skeletal muscle organoid produced from the cells of a human patient (e.g., an autograft) may be implanted at a first anatomical location for a defined period and subsequently implanted at a second location at or after the time of removal.

At least some of the cells of the organoid contain a foreign DNA sequence. The foreign DNA sequence may be extrachromosomal, integrated into the genomic DNA of the organoid cell, or may result from a mutation in the genomic DNA of the organoid cell. In addition, the cells of the organoid may contain multiple foreign DNA sequences. Moreover, the different cells of the organoid may contain different foreign DNA sequences. For example, in one embodiment, a skeletal muscle organoid may include myofibers containing a first foreign DNA sequence and fibroblasts containing a second foreign DNA sequence. Alternatively, the skeletal muscle organoid could include myoblasts from different cell lines, each cell line expressing a foreign DNA sequence encoding a different bioactive compound. These "mosaic" organoids allow the combined and/or synergistic effects of particular bioactive compounds to be exploited. For example, myoblasts expressing growth hormone may be combined with myoblasts expressing an insulin-like growth factor to produce organoids useful in stimulating muscle growth/regeneration. Similarly, myoblasts expressing a bone morphogenetic protein may be combined with myoblasts expressing a parathyroid hormone to produce organoids useful in stimulating bone and cartilage growth/regeneration.

In a preferred embodiment, the foreign DNA sequence encodes a protein which is the bioactive compound. The protein is produced by the cells and liberated from the organoid. Alternatively, the DNA sequence may encode an enzyme which mediates the production of a bioactive compound or a cell surface protein which enhances the uptake and metabolism of compounds from the host tissue or circulation (e.g., lactic acid or low density lipoproteins). The DNA sequence may also encode a DNA binding protein which regulates the transcription of the sequence encoding a bioactive compound or an anti-sense RNA which mediates translation of the mRNA for the bioactive compound. The DNA sequence may also bind trans-acting factors such that the transcription of the sequence (i.e., foreign or native) encoding the bioactive compound is enhanced (e.g., by disinhibition). Furthermore, the foreign DNA sequence may be a cis-acting control element such as a promoter or an enhancer coupled to a native or foreign coding sequence for the bioactive compound or for an enzyme which mediates the production of the bioactive compound. Thus, the foreign DNA sequence may be expressible in the cell type into which it is introduced and may encode a protein which is synthesized and which may be secreted by such cells. Alternatively, the foreign DNA sequence may be an element that regulates an expressible sequence in the cell.

EXEMPLIFICATION

Described below are examples of embodiments of the invention in which a gene of interest (e.g., encoding a protein of interest (or bioactive compound) rhGH, rhBMP, or rhIGF) is introduced into mammalian muscle cells (mouse myoblasts, primary neonatal rat skeletal myoblasts, or fetal human myoblasts) according to the invention. The cells containing the gene of interest are then manipulated and/or permitted to form organoids according to the invention, wherein the organoids are herein demonstrated to produce the protein of interest. The protein-producing organoids are implanted into a mammal and production of the bioactive compound in therapy is demonstrated.

Mammalian skeletal myoblasts are tissue engineered into organ-like structures (organoids) containing parallel arrays of organized myofibers.

The examples herein below demonstrate the making and using of an bioactive compound-producing organoid according to the invention using the following cells: primary neonatal rat skeletal myoblasts, C2C12 adult mouse myoblast cell line, or fetal human myoblasts (FIGS. 6A and B).

Figure 7:
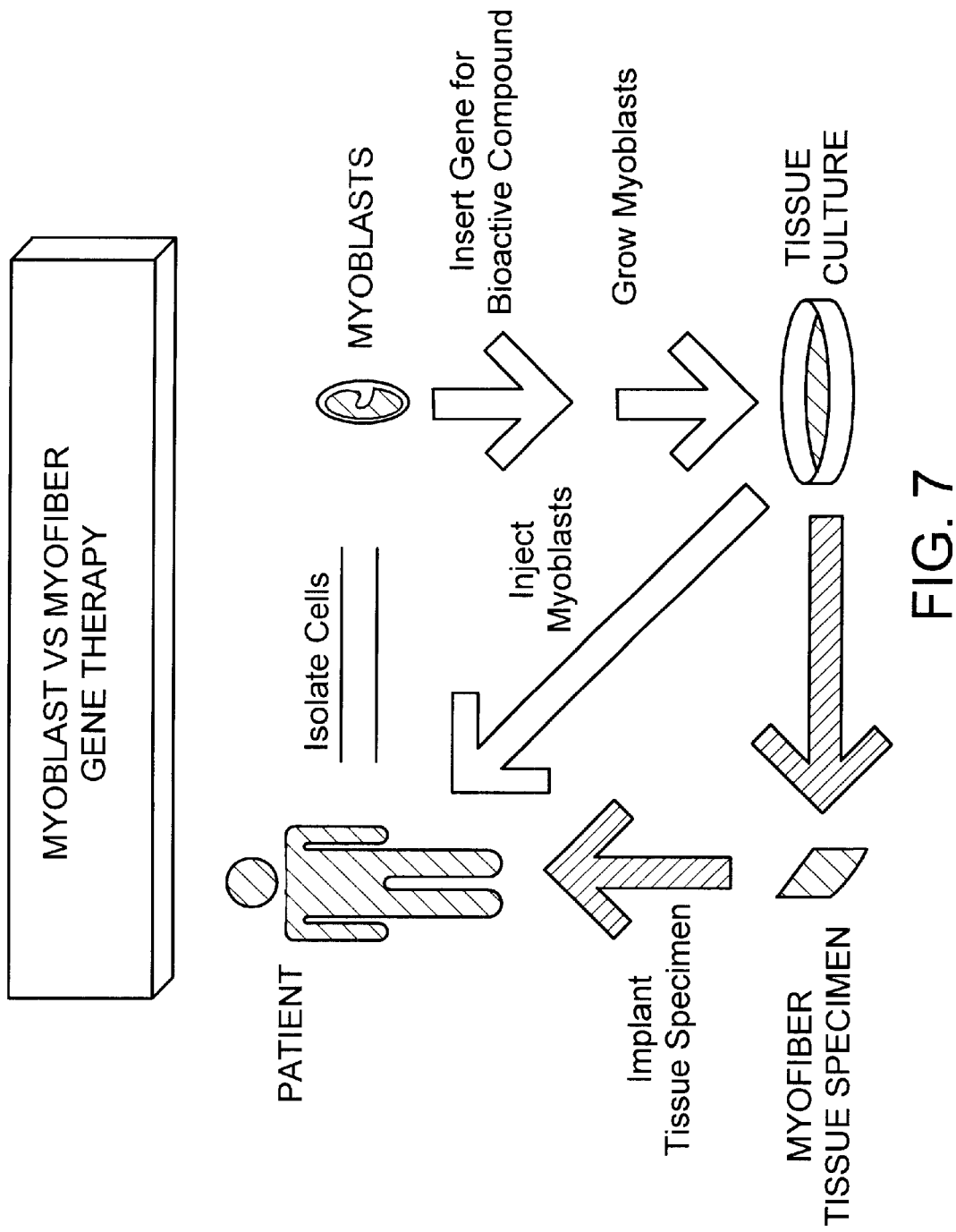
FIG. 7 is a flow chart comparing myoblast and myofiber gene therapy methods.

A. Delivery of Human Growth Hormone to Mice by Implanting Skeletal Muscle Organoids FIG. 7 shows an overview and comparison of myoblast and myofiber gene therapy. Both methods generally involve isolating myoblasts from a patient in need of gene therapy, inserting into the myoblasts a DNA sequence encoding a bioactive compound, and expanding the myoblast cell population by in vitro culturing. In contrast to myoblast gene therapy, the myoblasts used in myofiber gene therapy are further cultured in vitro under conditions which result in the formation of an organoid having in vivo-like gross and cellular morphology. The organoid is subsequently implanted into the patient to deliver the bioactive compound.

To carry out the delivery of a bioactive compound to an organism, skeletal muscle organoids were formed in vitro, as described above, from C2C12 mouse skeletal muscle myoblasts stably co-transfected with recombinant human growth hormone-expressing and β-galactosidase-expressing constructs. Prior to implantation, in vitro production of recombinant human growth hormone ("rhGH") was measured by radioimmunoassay according to the manufacturer's instructions (Nichols Institute Diagnostics, San Juan Capistrano, Calif.). Between three and twenty-four days of culture, the mean rhGH production ranged between 1.0 and 3.5 $\mu$g/day/organoid (see Table 1).

TABLE 1

IN VITRO PREIMPLANT SUMMARY

| Experiment | Date | Initial Cell # per organoid (× $10^6$) | Age of organoid (Days) | Mean rhGH ($\mu$g/day/ organoid) (N=) | Treatment of organoids |
|---|---|---|---|---|---|
| IMPLANT 1 | 8/24 | 6 | 3 | 1.9 (2) | none |
|  |  |  | 7 | 3.5 (2) |  |
| IMPLANT 2 | 9/21 | — | — | — | — |
| IMPLANT 3 | 10/5 | 4 | 7 | 1.7–2.8 (7) | none |
|  |  |  | 12 | 1.9–2.5 (6) |  |
| IMPLANT 4 | 10/20 | 2 | 21 | 2.2–2.6 (5) |  |
| IMPLANT 5 | 10/25 | 2 | 12 | 2.9 (12) | no cytosine arabinoside ("araC") |
|  |  |  | 12 | 2.0 (4) | 1 $\mu$g/ml araC for 4 days |
| IMPLANT 6 | 11/8 | 3 | 19 | 1.0 (6) | no araC |
|  |  |  |  | 1.0 (6) | 1 $\mu$g/ml araC for 5 days |
| IMPLANT 7 | 11/9 | 3 (non-rhGH secreting) | 17 | 0 (3) | control experiment |

TABLE 1-continued

IN VITRO PREIMPLANT SUMMARY

| Experiment | Date | Initial Cell # per organoid (x $10^6$) | Age of organoid (Days) | Mean rhGH ($\mu$g/day/ organoid) (N=) | Treatment of organoids |
|---|---|---|---|---|---|
| IMPLANT 8 | 11/3 | 2 | 14–20 | 1.5 to 2.2 (6) | no araC |
|  |  |  |  | 1.2 to 1.6 (6) | 1 $\mu$g/ml araC for 5 days |
| IMPLANT 9 | 11/30 | 1–2 | 24 | 1.7 to 2.4 (8) | 1 $\mu$g/ml araC for 8 days |
| IMPLANT 10 | 12/5 | 1.5–2.0 | 20 | 2.1 to 2.9 (14) | 1 $\mu$g/ml araC for 4 days |

The organoids were implanted into adult C3HeB/FeJ mice (i.e., syngeneic to C2C12 cells) by the following method. Mice were weighed to determine dosages of cyclosporine and anesthetic. One hour prior to the surgical implantation of the organoid, each mouse was given an injection of 60 mg/kg of cyclosporine A. Each mouse was then selected in turn and anesthetized by intramuscular injection of 55 mg/kg Ketamine, 1 mg/kg Promazine, and 5 mg/kg Xylazine. The site of implantation was then depilatated with Nair™ or by shaving, and prepped for aseptic surgery. For organoids implanted subcutaneously, a four to six centimeter long incision was made along the back, the organoid was implanted in either a free floating state or fixed under tension (e.g., attached to the tissue attachment surfaces), and the incision was closed with four to six sutures of 4.0-black silk.

For organoids implanted intramuscularly, a 15 to 30 millimeter incision was made parallel to the anterior tibialis muscle (e.g., anteriolateral aspect of the lower hind limb) to provide access to the muscle sheath. The anterior tibialis was gently split with forceps from tendon to tendon parallel to the muscle belly, thus providing a cavity for insertion of the organoid. The organoid was carefully removed from the vessel by prying the ends off the tissue attachment surfaces with sterile forceps and inserting it, under resting tension, in the implantation site. The incision was closed as described above. Mice were then followed post-surgically for distress and upon regaining consciousness were returned to a skeletal care facility. Cyclosporine injections are repeated daily for the duration of the experiment. The experimental protocol for the implantation of skeletal muscle organoids is summarized in Table 2 below.

TABLE 2

IN VIVO PROTOCOL SUMMARY

| Experiment | Date | Site of Implant | # of Surviving Skeletals | rhGH Producers (# and method) of implants) |
|---|---|---|---|---|
| IMPLANT 1 | 8/24 | intramuscular free-floating | 2 of 2 | 0 (1 free) |
| IMPLANT 2 | 9/21 | controls only - cyclosporine dose-response | 6 of 6 | no organoids implanted |
| IMPLANT 3 | 10/5 | subcutaneous free-floating | 3 of 4 | 1 (3C - 2 free) |
| IMPLANT 4 | 10/20 | subcutaneous fixed under tension | 2 of 3 | 2 (2D - 2 fixed) (3D- 1 fixed/1 free) |
| IMPLANT 5 | 10/25 | subcutaneous fixed under tension | 1 of 2 | 1 (1E - 3 fixed) |
| IMPLANT 6 | 11/8 | subcutaneous fixed under tension | 4 of 7 | 3 (6A, 6D, 6E - fixed) (6G - no organoid) |
| IMPLANT 7 | 11/9 | subcutaneous fixed under tension | 2 of 3 | 0 (7A and 7C - 1 fixed, non-rbGH secreting organoid) |
| IMPLANT 8 | 11/13 | subcutaneous fixed under tension | 5 of 8 | 4 (8C, 8D, 8F and 8G - 1 fixed) |
| IMPLANT 9 | 11/30 | subcutaneous fixed under tension or free-floating | 7 of 7 | 5 (9A, 9B, 9C, 9D and 9F - 1 fixed) 1 (9E - 1 free) (9G - no organoid) |
| IMPLANT 10 | 12/5 | subcutaneous fixed under tension | 7 of 11 | 7 (10A, 10B, 10C, 10D, 10F, 10G, and 10J - 1 fixed) |

Blood was collected every one to seven days by tail bleeding from the mice. Sera concentrations of rhGH were measured by radioimmunoassay according to the manufacturer's instructions (Nichols Institute Diagnostics, San Juan Capistrano, Calif.).

Figure 9B:
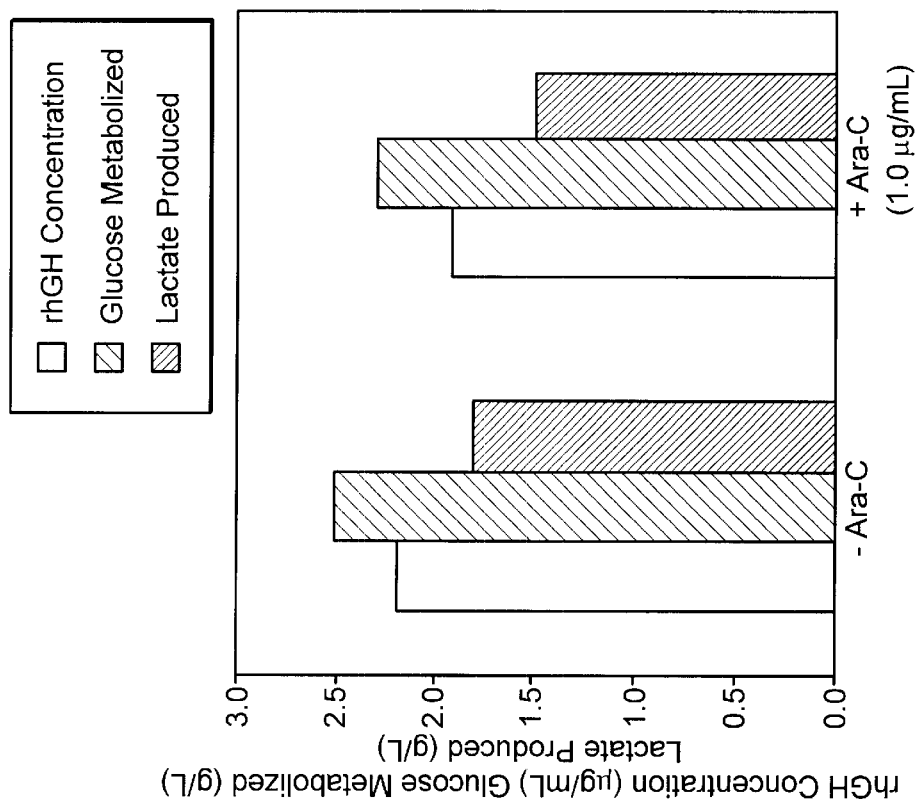
FIGS. 9A–9B are graphs of the effects of cytosine arabinoside on rhGH-secreting C2C12 proliferating myoblasts and post-mitotic myofibers.
Figure 9A:
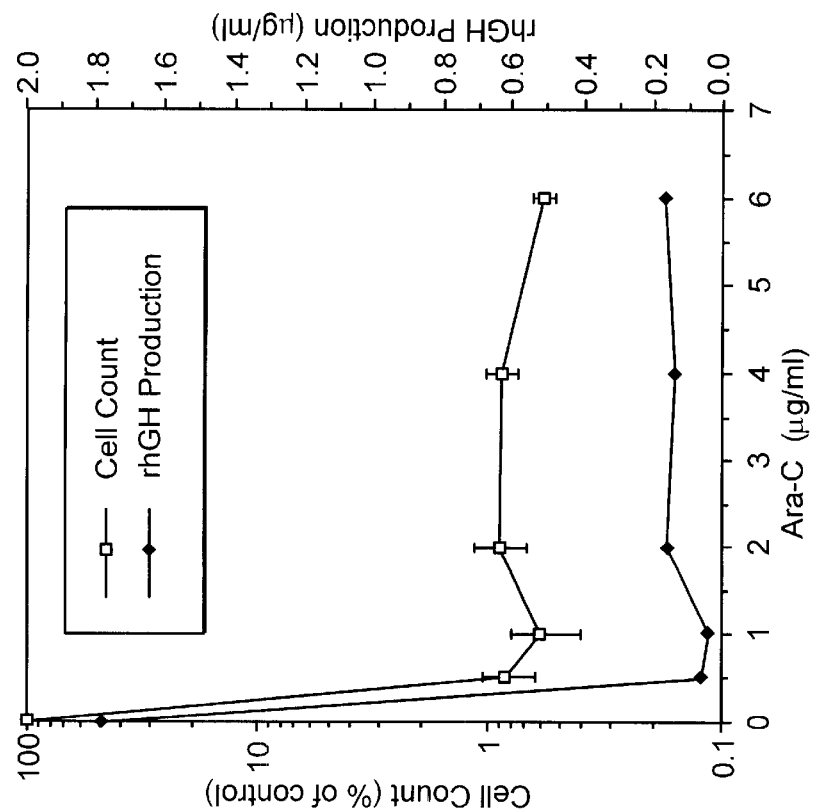

As shown in FIGS. 8A–8F, rhGH was detected in the blood of skeletals receiving rhGH organoid implants, but not in controls (6G, 7A, 7C, and 9G) for up to thirty-three days post-implantation. Serum concentrations were elevated as high as approximately 5.5 to 9 ng/ml in skeletals receiving multiple implants of rhGH producing organoids (1E, 2D), whereas serum from skeletals receiving no implant (6G, 9G)

or implants of non-rhGH secreting organoids (8A and 8C) contained no detectable rhGH. In addition, skeletals receiving organoids treated in vitro with cytosine arabinoside prior to implantation (1E, 6E, 8D, 8F, 8G, 9A through 9F, and 10A through 10J) demonstrated serum rhGH levels comparable to those of skeletals receiving implants which were not treated in vitro with cytosine arabinoside prior to implantation (i.e., 2D, 3C, 3D, 6A, 6D, and 8C). Under the conditions used in this study, cytosine arabinoside treatment kills greater than 99% of proliferating C2C12 myoblasts while having only a minor effect on myofiber metabolism and rhGH secretion (FIG. 9). Moreover, FIG. 10C shows that the rhGH gene and the β-galactosidase gene are only expressed in post-mitotic myofibers. These results demonstrate that organoids including substantially post-mitotic cells can deliver therapeutic levels of a bioactive compound for up to thirty-three days post-implantation.

Figure 10A:
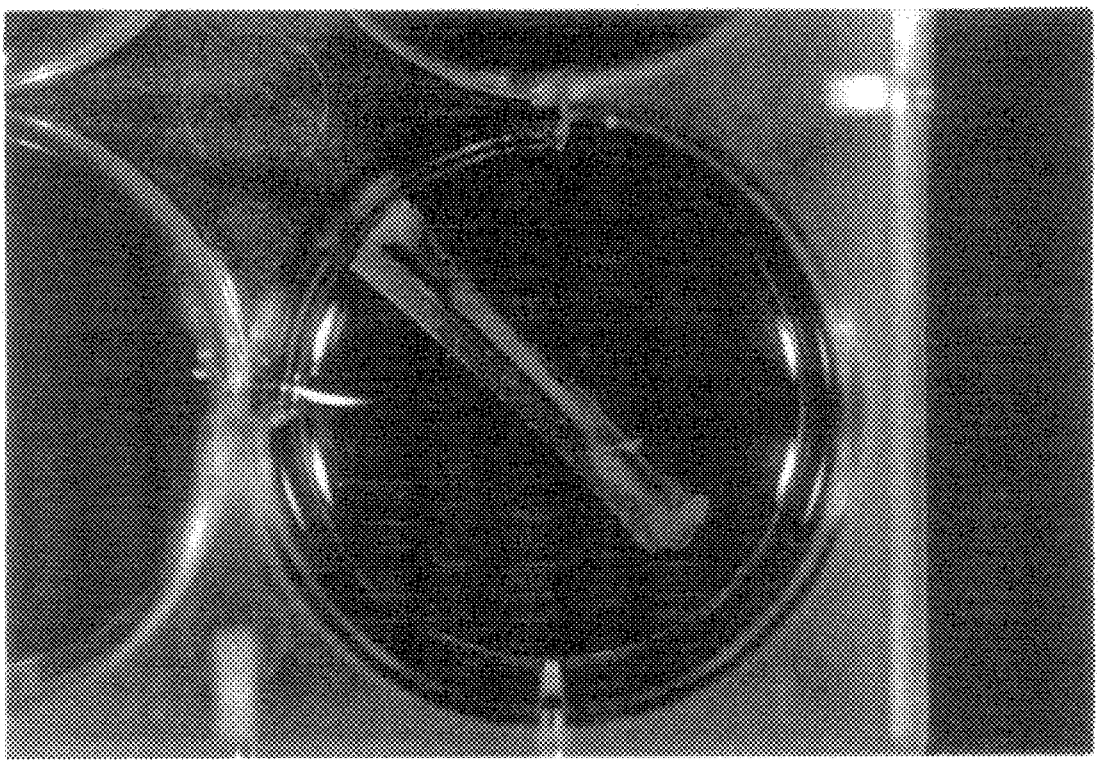
FIGS. 10A–10C are photographs of a skeletal muscle organoid grown in vitro from rhGH-secreting C2C12 cells, implanted in vivo, and subsequently removed and further cultured in vitro.
Figure 10B:
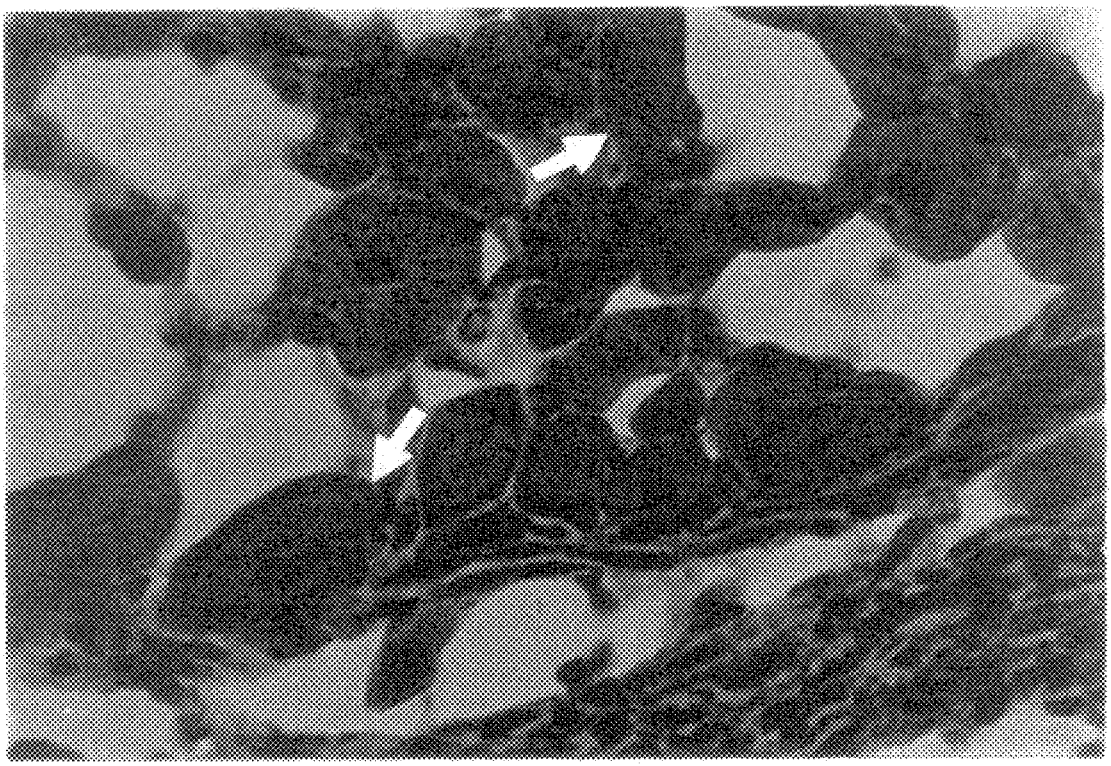
Figure 10C:
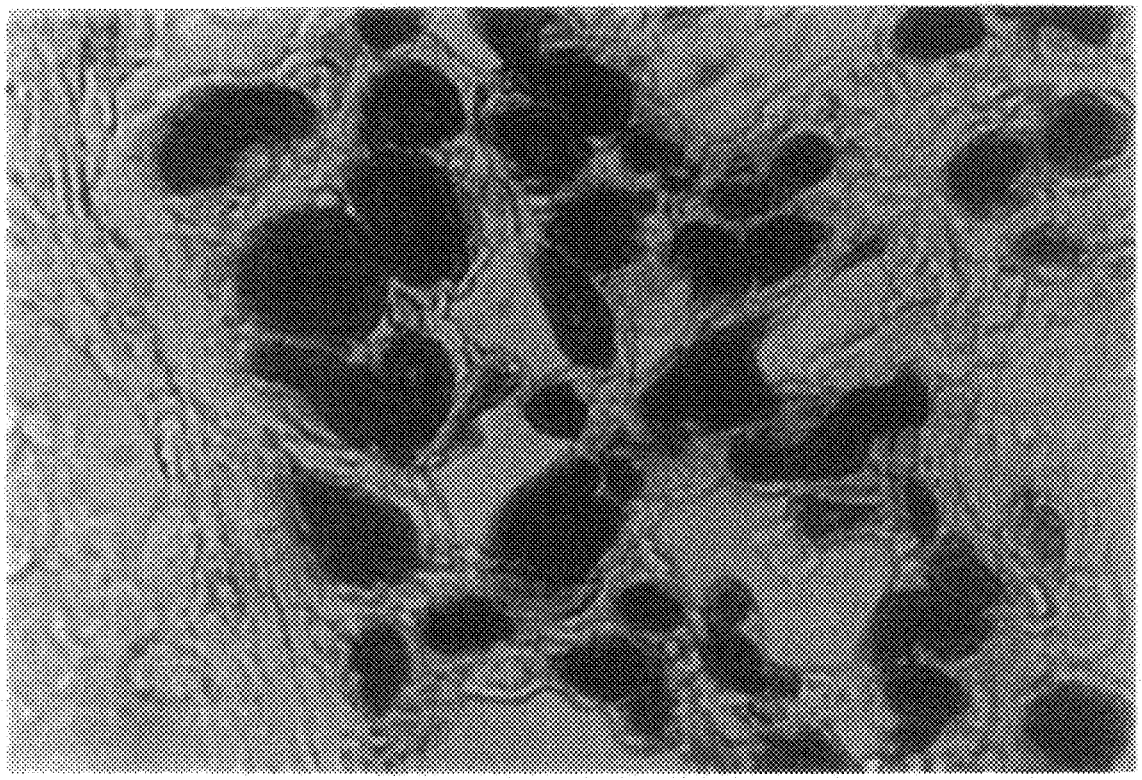

FIG. 10(A) rhGH secreting muscle organoid removed after 2 weeks in mouse 2D; (B) H&E stained cryostat cross-section of organoid shown in (A), with well differentiated myofibers running longitudinally in the organoid, and parallel to each other (arrows); and (C) X-gal blue staining of β-galactosidase activity in the cells containing the rhGH gene and β-gal gene (co-transfected in the same C2C12 myoblasts).

It is noteworthy that within forty-eight hours following the removal of implants (i.e., 8D, 8G and 9F), rhGH was undetectable in the sera of skeletals previously having serum concentrations as high as 2.6 ng/ml. These data demonstrate the reversibility of delivering bioactive compounds by this method. In addition, organoids removed from skeletals may be re-incubated in vitro (see e.g., FIG. 10A). For example, the two organoids implanted into skeletal 3D produced 188 ng/day of rhGH in vitro post-implantation. These data suggest the feasibility of removing organoids and subsequently reimplanting them such that bioactive compounds may be delivered during multiple treatment periods separated in time. Moreover, the data suggest the feasibility of transplanting sequentially, at different sites within the same organism, organoids functioning as paracrine organs.

The rhGH production of 188 ng/day in vitro by organoids from skeletal 3D and the in vivo serum levels of 1.0 ng/ml on day twenty-four (i.e., just prior to removal) suggest a 188-fold difference between organoid production and steady state circulating levels of rhGH in the skeletal. These results compare favorably to the 500-fold difference between rhGH concentrations delivered by direct subcutaneous injection and steady state circulating levels, (Yang et al., 1995, *Circulation* 92:262–267, (1000 µg/day rhGH by direct subcutaneous injection produced 2 µg/ml serum concentrations in rats). It is also noteworthy that the organoid maintained in vivo under tension produced approximately 144 ng/ml when placed in vitro on removal from the skeletal, while the free floating organoid produced only 40 ng/ml when placed in vitro on removal from the skeletal. In addition, an organoid implanted under no tension (9E) was a poorer producer of rhGH in vivo than those placed under tension (9A, 9B, 9C). These results suggest that maintaining organoids under tension enhances the production and delivery of bioactive compounds.

B. rhGH Secreted from C2-organoids is Biologically Active and Can Attenuate Muscle Atrophy in Hindlimb-unloaded Host Skeletal Muscle in vivo Murine C2C12 skeletal myoblasts stably transduced with the gene for rhGH using retroviral vectors were tissue engineered into implantable C2-organoids secreting pharmacological levels of rhGH in vitro, as described herein. The C2-organoids were subsequently treated with cytosine arabinoside to remove unfused proliferating myoblasts. When implanted subcutaneously under tension into syngeneic C3HeB/FeJ mice, rapid and stable appearance of physiological levels of rhGH in the serum occurred for greater than 12 weeks. The implanted C2-organoids are well vascularized by the host, and retain their preimplantation structure, allowing surgical removal. Removal of the implants leads to the rapid disappearance of rhGH from the sera. The rhGH released from the C2-organoids is biologically active, based on the down regulation of a GH-sensitive 20 kD protein made in the liver, and secreted as a major urinary protein [MUP] (Vandenburgh et al, 1997, *Methods in Molecular Medicine: Tissue Engineering.* J. Morgan and M. Yarmush eds., Humana Press, Tottowa, N.J.).

Figure 12A:
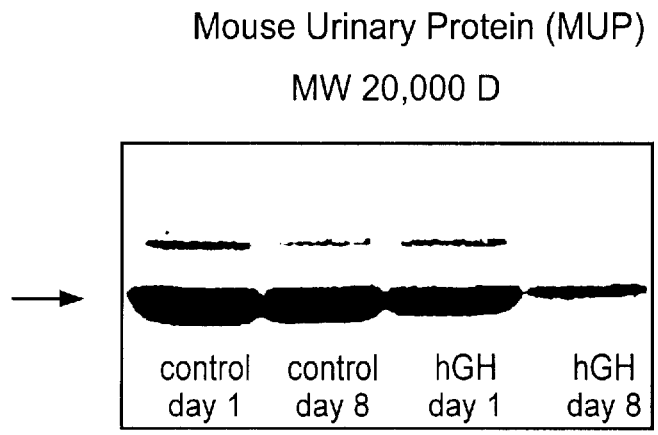
FIG. 12(A) is a polyacrylamide gel (left) of equal amounts of urine from C3HeB/FeJ mice implanted at Day 0 with either non-rhGH secreting (control) or rhGH-secreting C2-organoids (hGH); the arrow indicates the position of the 20 kD GH-sensitive liver protein MUP (major urinary protein).
Figure 12B:
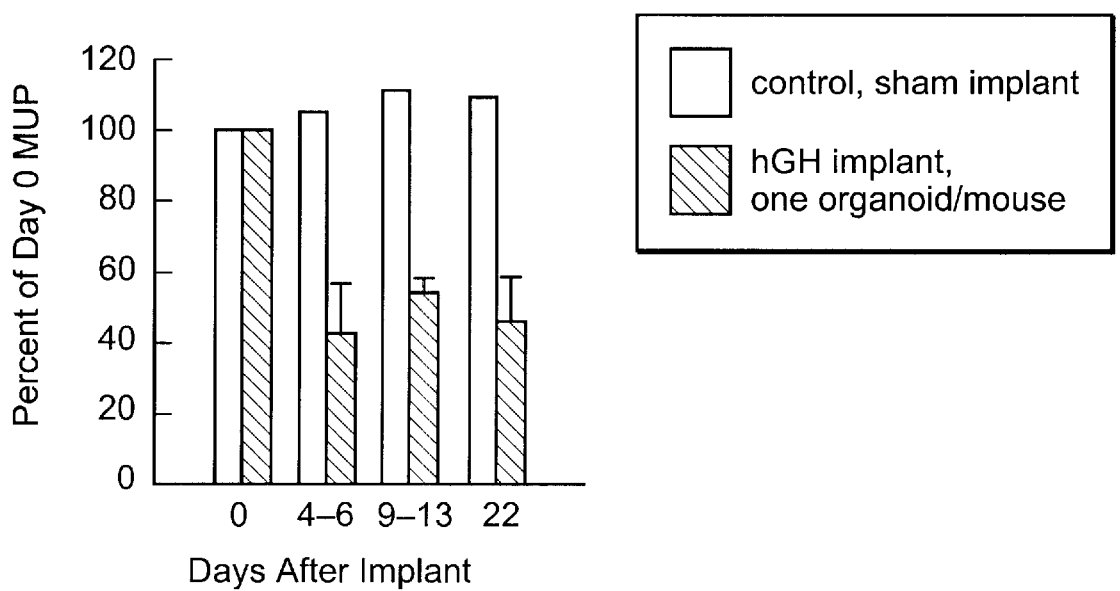
FIG. 12(B) is a bar graph showing results of a comparison of MUP levels in control and rhGH-secreting C2-organoids (hGH) at three weeks after implantation.

Animals implanted with rhGH secreting C2-organoids show a significant down regulation of MUP protein levels which lasts as long as the implant remains in the animal (FIGS. 12A, 12B). Removal of the implant leads to a return of MUP to preimplantation levels (data not shown). Organoids are thus effective for the long-term delivery of biologically active proteins such as rhGH. FIG. 12 demonstrates that rhGH secreted from muscle organoids is biologically active.

Figure 13C:
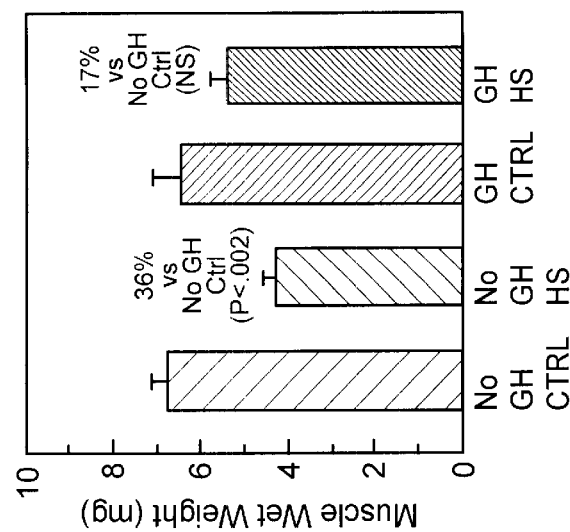
FIG. 13 contains bar graphs showing results of attenuation of hindlimb unloading-induced skeletal muscle atrophy with rhGH secreting C2-organoids. (A) and (B) are data for the plantaris muscle while (C) is data for the soleus muscle. Each value is the mean±SE of 3 to 6 animals and statistical analyses by unpaired t-tests.
Figure 13B:
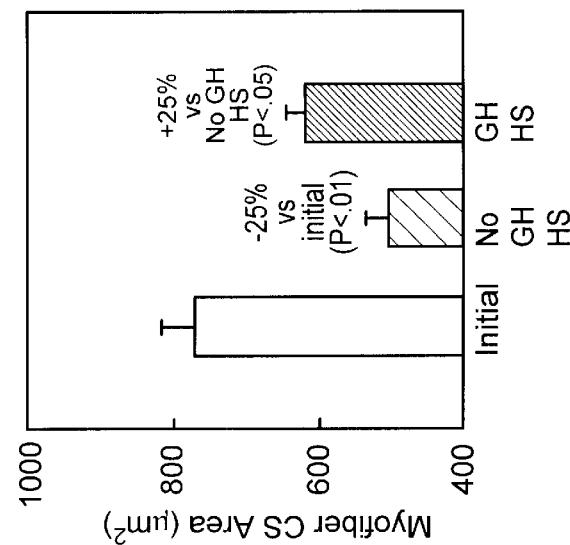
Figure 13A:
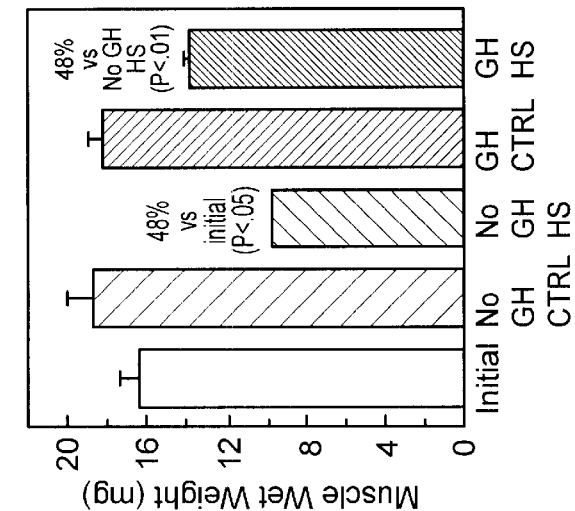

We have tested whether acute muscle wasting in a hindlimb unloaded mouse model can be reduced by rhGH-secreting C2-organoid implants (Vandenburgh et al, 1997, *Methods in Molecular Medicine: Tissue Engineering,* J. Morgan and M. Yarmush eds., supra). Initial studies were performed with the plantaris muscle since it is more growth hormone sensitive than the soleus (Aroniadou-Anderjaska et al., 1996, *Tissue Cell* 28:719–724; Grindeland et al., 1994, *Am. J. Physiol. Regul. Interg. Comp. Physiol.* 267:R316–R322). Based on both muscle wet weight (FIG. 13A) and myofiber cross sectional area (FIG. 13B), animals implanted with rhGH-secreting C2-organoids show significant attenuation of muscle wasting over a 6 day period compared to animals implanted with control, non-rhGH-secreting C2-organoids. Similar results have also been obtained in additional experiments with the less GH-sensitive soleus muscle (FIG. 13C). These studies support therapeutic efficacy since injected rhGH has been found to be effective in attenuating rat muscle wasting only in combination with moderate exercise. Delivery of continuously synthesized rhGH according to the invention may thus be more effective than daily rhGH injections since GH has a half life of less than 10 min in the circulation. In FIG. 13, six to eight week old C3HeB/FeJ mice were implanted with 2–3 C2-organoids per animal engineered from either normal C2C12 myoblasts or growth hormone (GH)-secreting C2C12 myoblasts. Each rhGH-secreting C2-organoid produced 1 to 3 µg rhGH per day preimplantation and a steady state serum level of 2–3 ng/ml from Day 1 to Day 8 after implantation. On Day 1 to 3 after implantation, half of the animals were hindlimb suspended (HS) for 5–8 days (n=3 to 6 per group). Hindlimb muscles were processed for wet weight and myofiber cross-sectional areas by standard protocols. (A) and (B) are data for the plantaris muscle while (C) is data for the soleus muscle. Each value is the mean±SE of 3 to 6 animals and statistical analyses by unpaired t-tests.

C. Primary Rat Neonatal Myoblast Tissue Engineered into Organoids

Primary Fisher 344 neonatal myoblasts organoids were recently engineered to release physiological levels of rhGH when transduced with a replication defective retroviral MFG-hGH expression vector (FIG. 6C).

Myofiber tension is an important regulator of rhGH secretion in these R-organoids (FIG. 6D), as described herein for C2 organoids.

Figure 11:
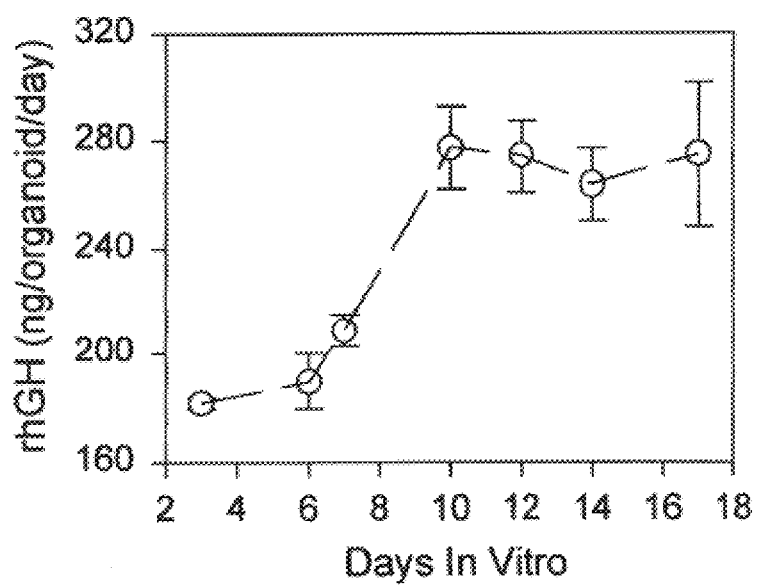
FIG. 11 is a graph of physiological levels of rhGH produced from primary adult rat myofibers transduced with replication defective retroviral vectors.

Adult rat myoblast isolation, rhX gene transduction, and organoid formation are performed as follows. Primary myoblasts were isolated by standard isolation procedures (Cantini et al., 1994, *In Vitro Cell Dev. Biol.*, 30A:131–133) from the tibialis anterior muscle of adult 120–150 g rats. Approximately $1 \times 10^6$ cells were isolated from one tibialis anterior muscle and expanded to $14 \times 10^6$ cells in 12–14 days. Twenty-five percent confluent myoblast cultures in T75 flasks were transduced with the MFG-hGH retroviral expression vector (FIG. 6C). When confluent, the transduced myoblasts were subcultured at a density of 100,000 cells/well and allowed to differentiate into myofibers. Cultures secreted 600–900 ng rhGH/$10^6$ cells/day (FIG. 11) a level comparable to the C2-organoids which were biologically active when implanted in adult mice (Vandenburgh et al., 1997, *Keystone Symposia on Mol. and Cellular Biol.*, In Press, (Abstr.)). R-organoids were also formed from these cells and maintained in vitro for 2–3 weeks. Adult rat myoblasts thus behave in a similar fashion to the neonatal rat myoblasts. The adult myoblast preparations have a significantly lower initial yield of cells per experiment (1 vs $100 \times 10^6$), and therefore a time period of approximately several extra weeks is necessary if adult cells are used. In FIG. 11, myoblasts were isolated from the tibialis anterior muscle of adult rats and transduced with the MFG-hGH retroviral expression vector. After differentiation into myofibers, medium samples were removed, diluted 1:50, and assayed for rhGH by RIA. Each point is the mean±S.E. (N=4).

Figure 14:
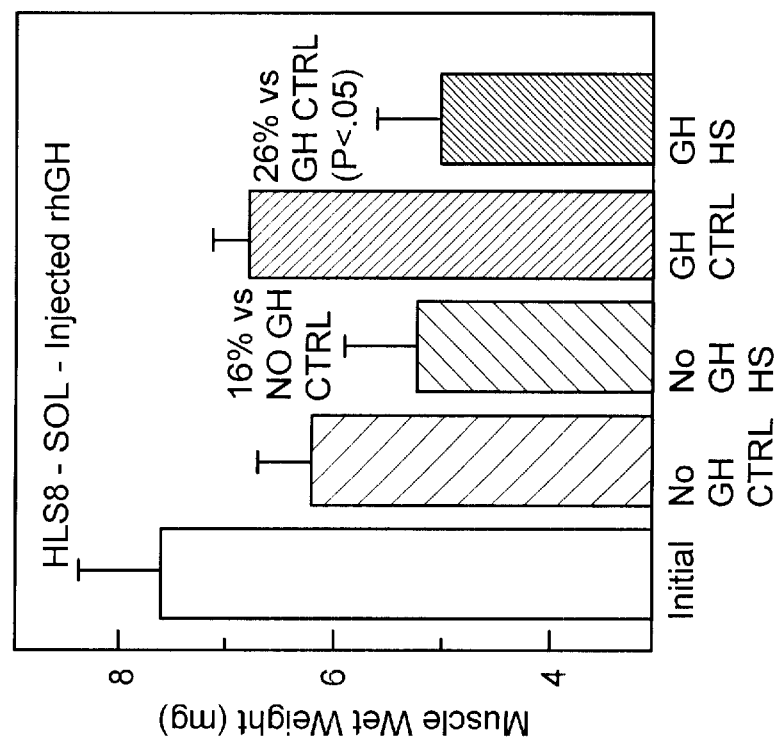
FIG. 14 contains bar graphs showing results of attenuation of hindlimb unloading-induced skeletal muscle atrophy in the plantaris but not the soleus muscle with daily rhGH injections.
Figure 14:
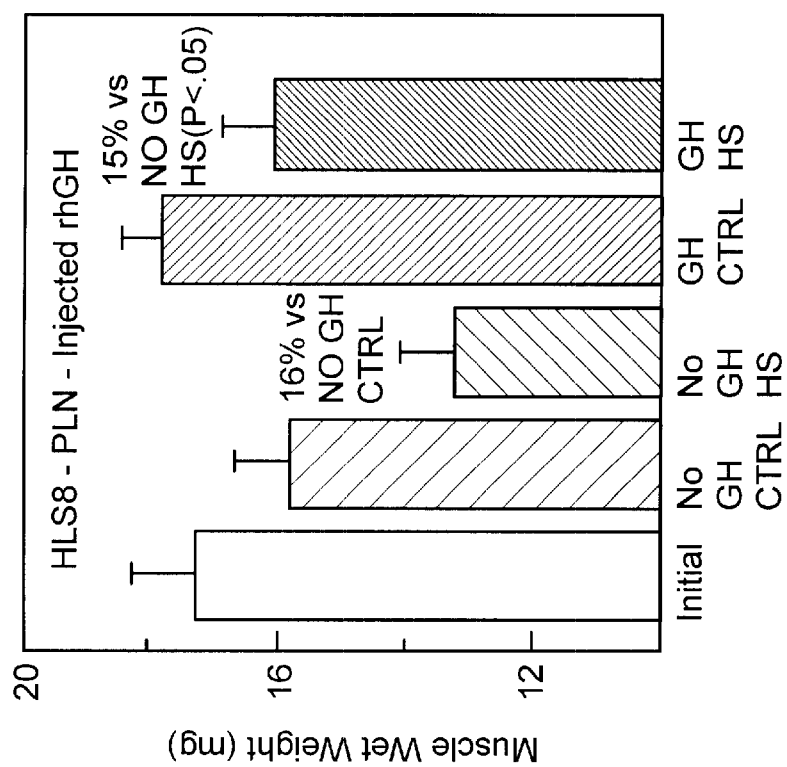

D. Delivery of rhGH According to the Invention is More Effective than Daily rhGH Injections in the Prevention of the Hindlimb Unloaded Atrophy of the Slow Soleus Muscle We injected purified rhGH (Genentech) daily to determine its ability to attenuate hindlimb unloaded muscle atrophy in mice. Unlike the results of others in rats indicating that injected rhGH alone could not attenuate hindlimb unloading-induced muscle atrophy (Grindeland et al., 1994, *Am. J. Physiol. Regul. Integr. Comp. Physiol.* 267:R316–R322; Linderman et al., 1994, *Am. J. Physiol. Integr. Comp. Physiol.* 267:R365–R37; Roy et al., 1996, *J. Appl. Physiol.* 81:302–311), we found in the mouse model that injected rhGH was effective in attenuating atrophy of the fast plantaris muscle (FIG. 14A), but not the slow soleus muscle (FIG. 14B). This may be due to the fact that slow muscles are less sensitive to the anabolic effects of rhGH than fast muscles (Aroniadou-Anderjaska et al., 1996, *Tissue Cell* 28:719–724; Grindeland et al., 1994, *Am. J. Physiol. Regul. Integr. Comp. Physiol.* 267:R316–R322). In contrast, rhGH-secreting C2-organoids were equally as effective in attenuating hindlimb unloaded muscle atrophy in both the fast plantaris and slow soleus muscles (FIG. 13A versus 13C). These results support the hypothesis that delivery of rhGH according to the invention is more effective than daily rhGH injections in treating atrophy of skeletal muscles. In FIG. 14, the experiments were performed in an identical fashion to those described above for FIG. 13, except that the animals were not implanted with C2-organoids but were injected daily with rhGH (1 mg/kg bodyweight) starting one day before hindlimb unloading. Each value is the mean±S.E. of 3–6 animals and statistical analyses by unpaired t-tests.

E. Delivery of Bone Morphogenetic Protein to an Organism by Implanting Skeletal Muscle Organoids 1. Transduction and Selection of C2C12 Myoblasts Expressing rhBMβ-6

ψ2 packaging cells producing high titers (>$1 \times 10^7$ pfu) of retrovirus containing the pLX(rhBMP-6)SN expression vector were provided by Dr. Vladimir Drozdoff, Department of Medicine, Vanderbilt University. Myoblast cell cultures, 50% confluent in T-75 flasks, were incubated for eight hours in 20 ml of conditioned media from the high viral titer packaging cells. The media was supplemented with 4 µg/ml of polybreen. After eight hours, the cells were placed in DMEM+10% fetal calf serum containing 2 µg/ml of polybreen, and cultured for an additional 48–72 hr, or until the cells had undergone one or two additional divisions. The transduced cells were then harvested, counted, and plated out as single cell clones in four 12-well plates. The single cell clones were selected by culturing in DMEM+10% fetal calf serum containing 400 µg/ml of G418. Single cell colonies began to appear after 2–3 weeks in culture. These colonies were first expanded to a single T-25 flask, and then expanded to two T-150 flasks which were grown to 90% confluency. The first flask was harvested for storage of cells in liquid nitrogen, and the second flask was processed for total RNA.

Alternatively, myoblasts are transducible by direct incubation with plasmids containing bone morphogenetic protein genes (e.g., mouse BMP-4, Fang et al., 1996, *Proc. Natl. Acad. Sci. U.S.A.* 93:5753–5758; human BMP-1, BMP-2A and BMP-3, Wozney et al., 1988, *Science* 242:1528–1532; human BMP-4, Ahrens et al., 1993, *DNA and Cell Biology* 32:871–880). For example, myoblasts may be successfully transduced by standard calcium phosphate coprecipitation or lipofection.

Figure 15A:
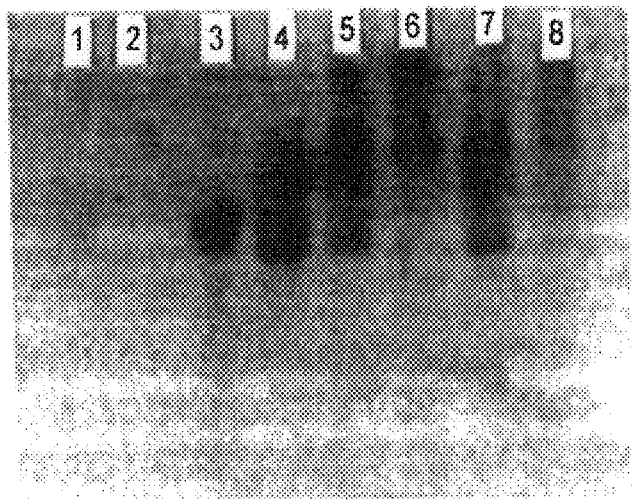
FIGS. 15A–15C are Northern blots of rhBMP-6 MRNA levels in C2C12 cells retrovirally-transduced with a rhBMP-6 gene.
Figure 15B:
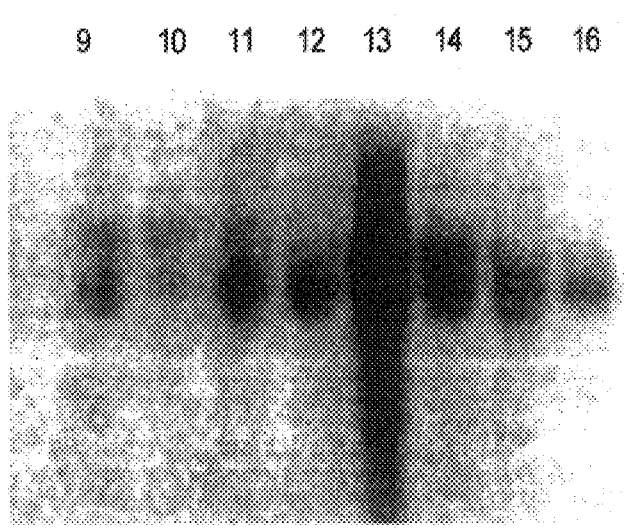
Figure 15C:
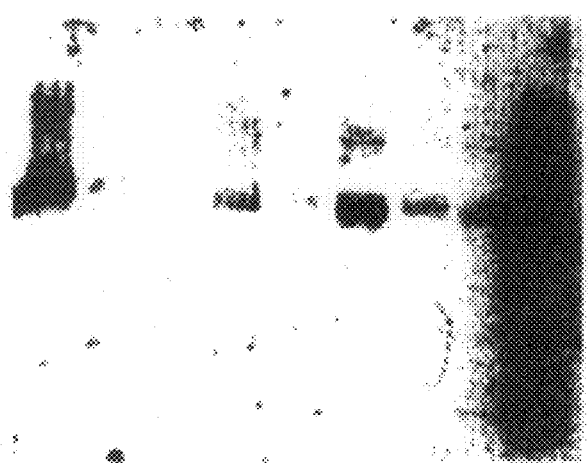

Northern blot analysis was performed on the cell clones with 20 µg of total or standard RNA per lane (FIGS. 15A–C). The blots were hybridized with a cDNA probe to rhBMP-6 (supplied by Genetics Institute, Cambridge, Mass.). Referring to FIGS. 15A and B, clones expressing high levels of rhBMP-6 mRNA (e.g., cell line 4A1 in lane 13 of FIG. 15B) were expanded and recloned from single cell colonies. Referring to FIG. 15C, subclones of cell line 4A1 were rescreened by Northern blot analysis, and clones 1A1 and 2A2 expressed high levels of rhBMP-6 MRNA relative to the other clones. Cell colonies retaining high expression of rhBMP-6 were harvested and banked in liquid nitrogen.

2. Expression of Biologically Active BMP-6

Figure 16:
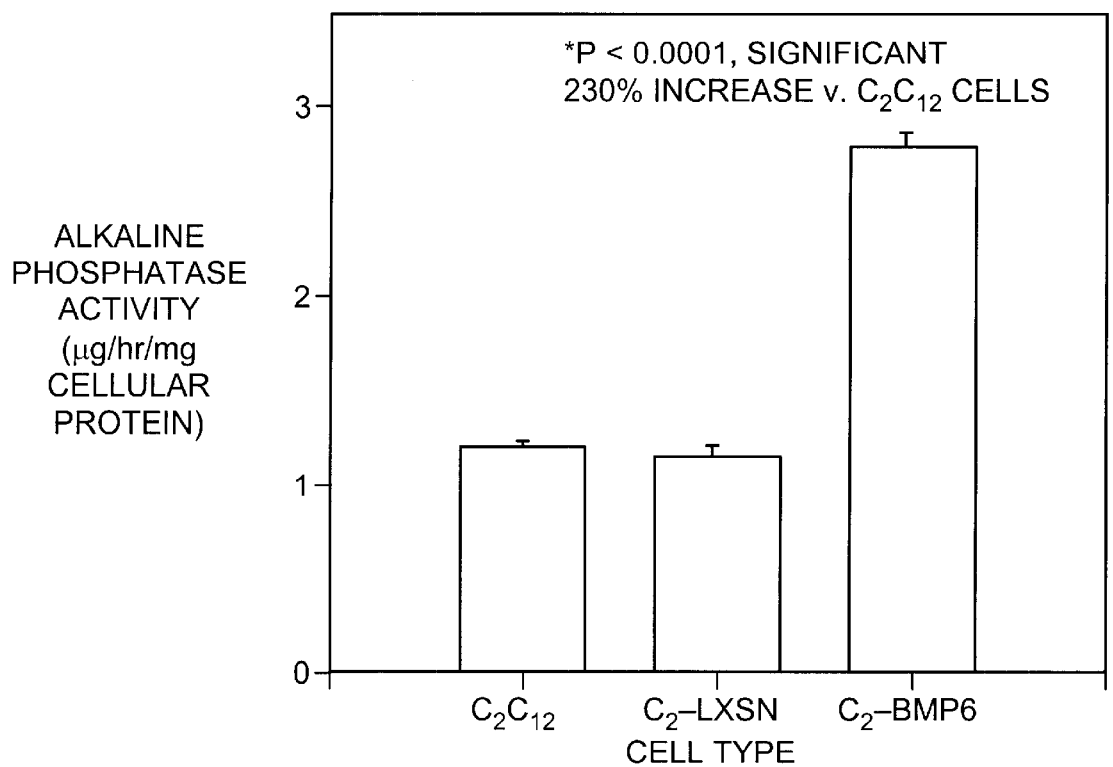
FIG. 16 is a graph of alkaline phosphatase activity in controls and C2C12 cells retrovirally-transduced with a rhBMP-6 gene.

The biological activity of rhBMP-6 in cell colonies retaining high expression of rhBMP-6 (i.e., $C_2$-BMP6 cells) was determined by measuring alkaline phosphatase activity (i.e., an osteoblastic marker) in the cells after 14 days in culture (FIG. 16). Normal C2C12 cells (i.e., non-transduced cells) and C2C12 cells transduced with the LXSN vector alone (i.e., $C_2$-LXSN cells) were used as controls.

Cells were harvested after 14 days as follows. Wells containing the cells were rinsed with phosphate buffered saline (0.1 m, pH 7.4; PBS) and then typsinized with five drops per well of 0.05% trypsin/EDTA solution in PBS. The trypsin/EDTA was neutralized with 500 µl serum-containing media per well, and cells were transferred to microcentrifuge tubes and centrifuged at 900 rpm for four minutes to pellet the cells. Cell pellets were resuspended and lysed in 500 µl of TXM buffer (10 mM Tris HCL; 1.0 mM magnesium chloride; 0.02 mM zinc chloride; 0.1% Triton X-100; and 0.02% sodium azide), and stored at −20° C. until assayed or assayed immediately for alkaline phosphatase activity as follows.

One hundred microliters of cell lysate, blank (buffer minus substrate), or standard (5 mM p-nitrophenol in buffer) was added to a tube containing 400 µl of alkaline phosphate assay substrate and buffer (0.1 mg glycine; 2.0 mM magnesium chloride; 2 mg/ml p-nitrophenyl phosphate) and incubated at 37° C. for 30 min. The reaction was stopped by adding 500 µl of 0.25 N NaOH, and the optical density at 410 nm was read on a spectrophotometer. The total cellular protein in each sample was measured with a Bio-Rad™ protein assay essentially according to the manufacturer's instructions (Bio-Rad Laboratories, Hercules, Calif.) and alkaline phosphatase activities calculated as follows:

$$\text{Total Alkaline Phosphatase Activity for Sample} \left[\frac{\mu g}{\text{hour}}\right] = \frac{(2 \times \text{Sample Optical Density} \times \text{Dilution Factor})}{(\text{Average of Standard Optical Densities})}$$

$$\text{Alkaline Phosphatase Activity} \left[\frac{\mu g/\text{hour}}{\text{mg cellular protein}}\right] = \frac{\text{Total Alkaline Phosphatase Activity for Sample}}{\text{Total Cellular Protein for Sample}}$$

3. Delivery of BMP-6 by Implanting skeletal Muscle organoids

The ability of $C_2$-BMP6 cells to differentiate and fuse to form skeletal muscle myofibers was analyzed by morphometric analysis and expression of the muscle-specific protein sarcomeric tropomyosin after six to fourteen days in culture. Normal C2C12 cells and $C_2$-LXSN cells were used as controls.

Normal C2C12 cells, $C_2$-LXSN cells, and C2-BMP6 cells were cultured separately in T-75 flasks. At 80% confluence, all cell types were individually subcultured and plated into four well-plates (i.e., 15-mm diameter wells pretreated with a collagen spray 1 mg/ml of rat-tail collagen, type I in 1% acetic acid). The cells were plated at a density of 100,000 cells per well in 750 µl of growth medium (DMEM-high glucose; 10% calf serum; 10% fetal calf serum; 100 units/ml penicillin; and 0.1 mg/ml streptomycin) and incubated in a humidified, 37° C., 5% $CO_2$ atmosphere.

The cells were fed 750 µl warm growth medium per well every 48 hours (i.e., day 2 and day 4 post-plating). Five days post-plating when all groups showed ~100% confluence, the cells were switched to a low serum fusion medium to promote fusion (DMEM-high glucose; 2% horse serum; 100 units/ml penicillin; 0.1 mg/ml streptomycin). The cells were fed fusion medium on days six, eight and ten post-plating. On day 12 post-plating, the cells were switched to a maintenance medium (DMEM-high glucose; 10% horse serum; 5% fetal calf serum; 100 units/ml penicillin; and 0.1 mg/ml streptomycin). The experiment was terminated on day 14.

Plates were fixed for morphometric analysis 6, 8, 12 and 14 days post-plating as follows. Cells were quickly rinsed twice with Eagle's balanced salt solution (EBSS), fixed with Histochoice™ for thirty minutes at room temperature, and incubated twice for ten-minutes in EBSS. The samples were then stored in fresh EBSS at 4° C. until used for immunohistochemical analysis.

From storage, samples were warmed to room temperature and rinsed with phosphate buffer saline (PBS; 10 mM, pH 7.4). Samples were then incubated with the primary antibody, anti-sarcomeric tropomyosin (1:100 dilution) in 0.5% Tween 20/PBS for thirty minutes at room temperature, followed by PBS rinsing. Secondary antibody and avidin biotinylated enzyme steps were performed essentially according to the Vectastain® Elite ABC Kit protocol. Samples were then developed with diaminobenzidine tetrahydrochloride (DAB) reagent to produce a brown precipitate, and then lightly counterstained with hematoxylin.

Figure 17A:
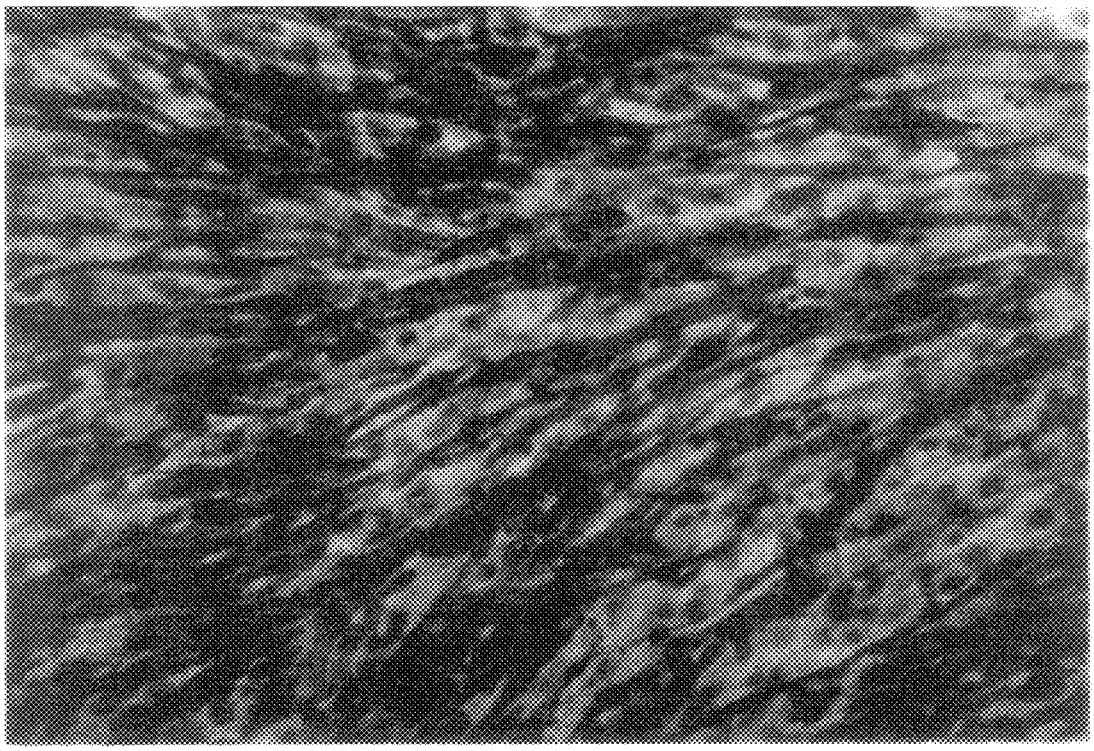
FIGS. 17A and 17B are micrographs of C2C12 cells retrovirally-transduced with a rhBMP-6 gene which have been stained for sarcomeric tropomyosin.
Figure 17B:
Figure 18A:
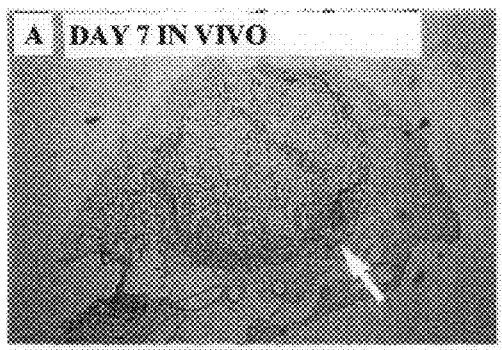
FIG. 18 are photographs of cross-sections of R-organoids implanted in adult Fisher 344 rats stained for sarcomeric tropomyosin. Long arrows indicate the surface of the implanted R-organoids, while shorter arrows indicate internal myofibers. (A) and (B) are 7 days postimplantation. Magnification is approximately 12× in (A) and 120× in (B), (C) and (D).
Figure 18B:
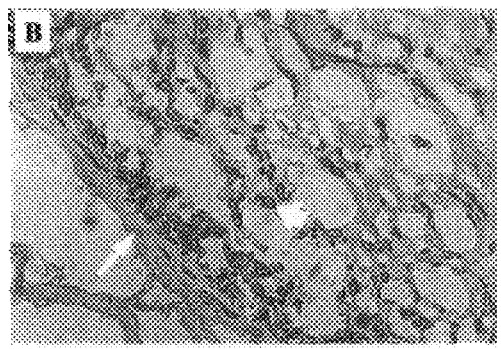
Figure 18C:
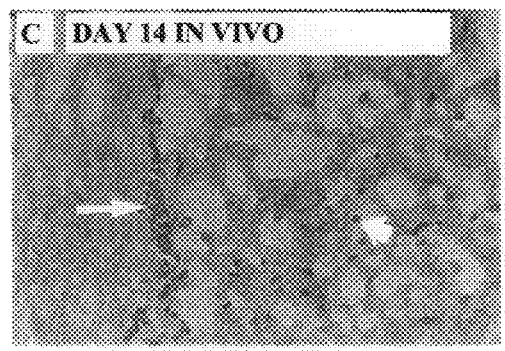
Figure 18D:
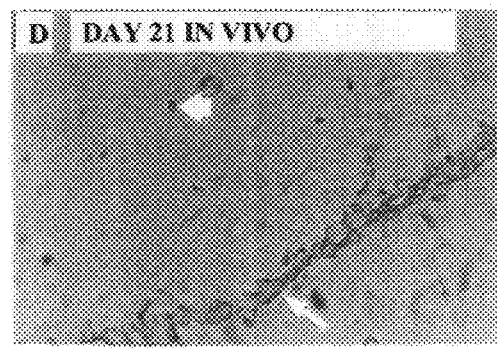

Referring to FIGS. 17A (Day 8 post-plating) and 17B (Day 14 post-plating), the ability of $C_2$-BMP6 cells to differentiate and fuse to form skeletal muscle myofibers is demonstrated by morphometric analysis (i.e., the presence of longitudinally-oriented multinucleated fibers) and by the presence of sarcomeric tropomyosin (i.e., a muscle-specific protein expressed in differentiated skeletal muscle myofibers but not in undifferentiated, proliferative myoblasts). Because the expression of a biologically active bone morphogenetic protein does not impair the ability of skeletal muscle myoblasts to differentiate and fuse to form skeletal muscle myofibers, skeletal muscle organoids which express bone morphogenetic proteins are produced as described above (see Section I), and are used to deliver bone morphogenetic proteins to an organism also as described above (see Section II).

Because bone morphogenetic proteins are extracellular molecules, skeletal muscle organoid delivery of the protein may be through endocrine, autocrine, or paracrine mechanisms. In a preferred embodiment, the organoid may function as a paracrine organ to deliver a bone morphogenetic protein to chondroblastic or osteoblastic precursor cells. For example, a skeletal muscle organoid expressing a bone morphogenetic protein may be implanted adjacent a non-union fracture to stimulate endochondral bone formation and repair. Alternatively, a skeletal muscle organoid could be implanted in an organism adjacent skeletal tissues which are susceptible to degeneration and fracture consequent to aging (e.g., the hip joint or spinal column of elderly humans). Similarly, bone morphogenetic protein expressing organoids may be employed to treat systemic or regional osteoporosis (e.g., of the spine, femoral neck, and scapular regions of elderly humans). Skeletal muscle organoids expressing bone morphogenetic proteins may also function to accelerate cartilage repair and the healing of segmental defects or bony fusions.

F. Transduction of C2C12 Muscle Cells to Secrete rhIGF-1

C2C12 mouse myoblasts were transduced with the MFG-IGF-1 retroviral transduction vector. The vectors described herein contain the gene of interest (rhGH or rhIGF-1) under the control of the viral Long Terminal Repeat promoter.

Utilizing an immunocytochemical staining technique for IGF-1, approximately 60% of the cells were transduced. The transduced cells were differentiated into muscle fibers and found to secrete 10 fold higher levels of IGF-1 than non-transduced cells (6.05±1.3 versus 0.49±0.11 ng/mL, $P<0.05$). These data shown the ability to genetically engineer myoblasts to secrete therapeutic proteins other than rhGH.

G. Human Myoblast Isolation, Tissue Culturing, and Organoid Formation Using Adult Human Biopsied Skeletal Muscle Standard muscle biopsies were performed on two adult male volunteers and myoblasts isolated by standard tissue culture techniques (Webster et al., 1990, *Somatic Cell and Mol. Gen.* 16:557–565). One hundred muscle stem cells (myoblasts) were identified from each biopsy by immunocytochemical staining with an antibody against desmin and the myoblasts were expanded through at least 30 doubling. The 100 myoblasts could thus be expanded into greater than 50 billion cells ($5 \times 10^{10}$). If these adult human myoblasts are transduced with the MFG-hGH retroviral vector to the same efficiency as the adult rat myoblast shown in #8 above, approximately $1 \times 10^8$ of these human myoblasts would be required to raise steady state human serum levels of rhGH to 5–7 ng/mL, a level equivalent to that found in normal adults (Harvey et al., 1995, *Growth Hormone Release:Profiles.*, S.

Harvey, C. G. Scanes and W. H. Daughaday, eds., CRC Press, Boca Raton, 193–223). In contrast, GH-deficient elderly have basal GH serum levels around 1.5 ng/mL (Harvey et al., 1995, *Growth Hormone Release:Profiles.,* S. Harvey, C. G. Scanes and W. H. Daughaday, eds., CRC Press, Boca Raton, 193–223). This is well within the organoid technology's capability.

Figure 19:
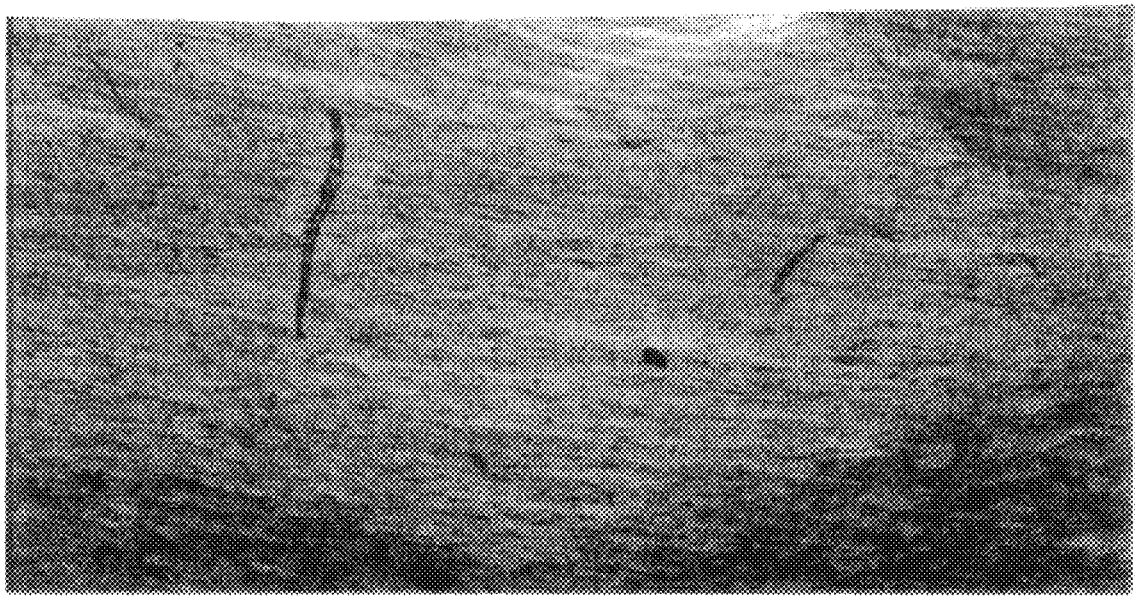
FIG. 19 is a photograph of bioartificial muscles (organoids) engineered from human adult myoblasts stained with an antibody to sarcomeric tropomyosin to show the organized muscle fibers.

Two million adult human myoblasts were tissue engineered into human organoids (H-organoids) which were very similar in appearance to the C2-organoids and R-organoids described in 1. above (FIG. 19). These H-organoids can be maintained in vitro for at least 2 weeks.

H. Transduction of Fetal Human Myoblasts with MFG-hGH

Human fetal skeletal myoblasts were purchased from a commercial source (Clonetics, Inc.) and transduced with MFG-hGH retroviral expression vector. The myoblasts were differentiated into myofibers and their secretion of rhGH assayed over an 11 day period. The cells secreted very high levels of rhGH (2–3 ug rhGh/$10^6$ cells/day), which were equivalent to the rate of secretion by the C2C12 myoblasts used previously for in vivo attenuation of skeletal muscle wasting. These data lead one of skill in the art to conclude that human myoblasts can be genetically engineered to secrete therapeutic levels of rhGH.

I. R-organoids Survive when Implanted subQ into Inbred Fisher 344 Adults

We have found that differentiated R-organoid myofibers implanted subQ into adult Fisher 344 rats survive for at least five weeks in vivo (FIG. 18). Myofiber survival is greatest on the surface of the implant (FIG. 18D), probably because capillaries do not infiltrate into the interior of the R-organoids until after four weeks (data not shown). By five weeks in vivo, the surface myofibers in the organoids have hypertrophied at least 3-fold compared to three week myofibers (data not shown). One possible mechanism to stimulate more rapid capillary in-growth into the R-organoids is by expressing vascular endothelial growth factor (VEGF) in the R-organoids using transient transfections with VEGF plasmids (Tsurumi et al., 1996, *Circulation* 94:3281–3290).

Dosage and Therapy

Figure 20B:
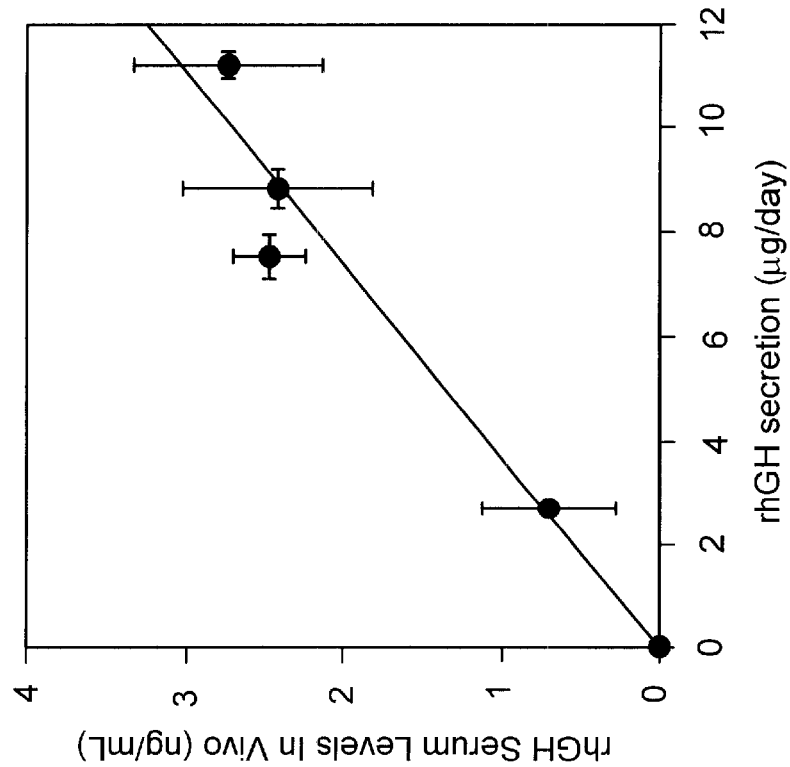
FIG. 20(B) is a graph of in vivo rhGH serum levels from rhGH levels secreted in vitro where the number of C2-organoids implanted per animal was varied from one to four.
Figure 20A:
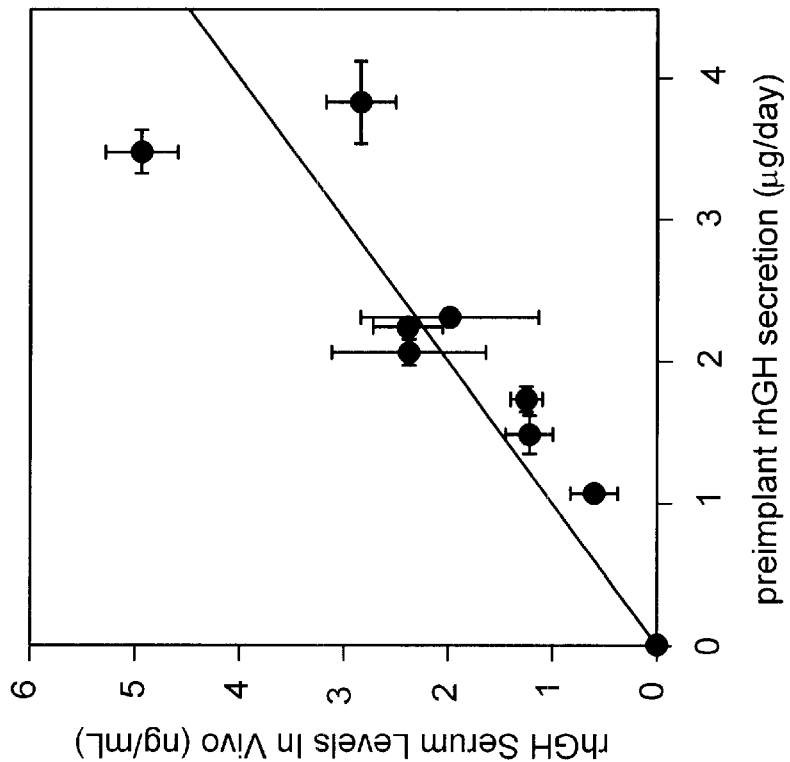
FIG. 20(A) is a graph of in vivo rhGH serum levels from rhGH levels secreted in vitro from C2-organoids engineered to contain different numbers of rhGH-secreting myofibers and one organoid per animal was implanted.

One of the major disadvantages of delivery of foreign proteins produced from injected genetically engineered cell is the great variability in the number of cells which survive from individual to individual and therefore the unpredictability of the delivery dose. The invention confers an advantage in terms of predictability of dosage. With genetically engineered organoids, the protein secretion levels can be monitored preimplantation in vitro. Accurate correlations can be made on in vivo serum levels of rhGH based on the preimplantation in vitro C2-organoid secretion levels (FIG. 20). In order to correlate the delivery dose of an organoid implanted in vivo for treatment according to the invention, organoid protein secretion levels (e.g., C2-organoid rhGH) can be varied by engineering a protein-producing organoid (e.g., C2-organoids) with different numbers of protein-secreting myofibers. In addition, varying numbers of organoids can be implanted and levels of bioactive compound determined. For C2-organoids, one to four organoids were implanted per animal, and a corresponding increase in the level of bioactive compound (rhGH) was found. Therefore, two protocols are provided for controlling protein delivery dose from organoids over an approximately 10 fold range; i.e., the selection of a number of bioactive compound-secreting cells for implantation and the selection of a number of bioactive compound secreting organoids for implantation. In FIGS. 20 (A and B), therefore, a correlation is shown of in vivo rhGH serum levels from rhGH levels secreted in vitro. A linear relationship exists for the amount of rhGH secreted by C2-organoids preimplantation and postimplantation.

The invention is applicable to therapies in which one or more bioactive compounds are delivered to an organism, for example, a mammal in therapeutically effective levels. A therapeutic gene is one which is expressible in a mammalian, preferably a human, cell and encodes RNA or a polypeptide that is of therapeutic benefit to a mammal, preferably a human. A vector may also include marker genes, such as drug resistance genes, the β-galactosidase gene, the dihydrofolate reductase gene, and the chloramphenicol acetyl transferase gene. A therapeutic effect is evident, for example, where the therapeutic gene encodes a product of physiological importance, such as replacement of a defective gene or an additional potentially beneficial gene function, is expected to confer long term genetic modification of the cells and be effective in the treatment of disease.

As discussed above, the dosages of a bioactive compound administered according to the invention will vary from patient to patient; a "therapeutically effective dose" will be determined by the level of enhancement of function of the transferred genetic material balanced against any risk or deleterious side effects. Monitoring levels of gene introduction, gene expression and/or the presence or levels of the encoded product will assist in selecting and adjusting the dosages administered. Generally, a composition including a bioactive compound-producing organoid according to the invention will be administered in a single dose (per time period in which the organoid implant is judged to be effective in producing the bioactive compound), such that the bioactive compound is produced in the mammal in the range of 1 ng–100 ug/kg body weight, preferably in the range of 100 ng–10 ug/kg body weight, depending upon the nature of the bioactive compound, its half-life, and its biological effect.

OTHER EMBODIMENTS

The above description is not intended to limit the invention either in spirit or scope. Other embodiments are within the following claims.

What is claimed is:

1. An organized tissue, comprising:
   a plurality of substantially post-mitotic cells, wherein at least a subset of said cells form an organized tissue approximating the in vivo gross morphology of a tissue of interest, said subset of cells comprising cells having a foreign DNA sequence operably linked to a promoter and encoding a protein of a type or produced in an amount not produced normally by said tissue of interest, wherein the protein is produced at detectable levels in said organized tissue.

2. The organized tissue of claim 1, wherein said subset of cells comprise skeletal muscle.

3. An organized tissue attached to the surface of a substrate, comprising:
   a plurality of substantially post-mitotic cells, wherein at least a subset of said cells form an organized tissue approximating the in vivo gross morphology of a tissue of interest, said subset of cells comprising cells having a foreign DNA sequence operably linked to a promoter and encoding a protein of a type or produced in an amount not produced normally by said tissue of interest; and
   a substrate having first and second tissue attachment surfaces, wherein the organized tissue comprises a first end and a second end adherent to, respectively, said first and second tissue attachment surfaces and wherein tension is maintained between said first and second ends of said organized tissue such that upon detachment of said tissue from one of the tissue attachment surfaces said tissue undergoes a contraction.

4. The organized tissue attached to the surface of a substrate of claim 3 wherein upon detachment of said tissue from one of said tissue attachment surfaces and said contraction of said organized tissue, said tissue produces an amount of protein that is less than the amount produced when tension is maintained between said first and second ends of said organized tissue, wherein the protein is produced at detectable levels in said organized tissue.

5. The organized tissue attached to the surface of a substrate of claim 3, said substrate being selected from the group consisting of metal or plastic.

6. The organized tissue attached to the surface of a substrate of claim 5, said metal substrate being steel mesh having a longitudinal axis and first and second points for attachment, and wherein said first and second attachment sites of said tissue are attached, respectively, to said first and second ends of said organized tissue.

7. An organized tissue comprising a plurality of substantially post-mitotic cells, wherein at least a subset of cells form an organized tissue approximating the in vivo gross morphology of tissue of interest that is retained upon implantation of said tissue in to a mammal, said tissue producing a protein of a type or in an amount not normally produced by a tissue of interest, said subset of cells comprising a foreign DNA sequence operably linked to a promoter and encoding a protein, and wherein the organized tissue is further comprised of substantially post-mitotic cells, and wherein the protein is produced to detectable levels in said tissue.

8. An in vitro method for producing an organized tissue, comprising the steps of: providing cells of a tissue of interest, wherein at least a subset of said cells comprise a foreign DNA sequence operably linked to a promoter and encoding a protein, wherein said cells of said tissue of interest are mixed with an extracellular matrix to create a suspension;

placing said suspension in a vessel having first and second tissue attachment surfaces thereon, wherein the tissue attachment surfaces are positioned such that as the tissue forms in vitro from said cells of said tissue of interest, said cells of said tissue of interest may adhere to said first and second attachment surfaces and align between said attachment surfaces and;

allowing the suspension to coalesce; and culturing said coalesced suspension under conditions in which said organized tissue forms such that said cells form an organized tissue approximating the in vivo gross morphology of said tissue of interest and wherein the organized tissue forms such that a first end and a second end adheres to said tissue attachment surfaces, and wherein tension is maintained between the first and second ends of said organized tissue such that upon detachment of said tissue from one of the tissue attachment surfaces said tissue undergoes a contraction.

9. An in vivo method for producing a protein encoded by cells of an organized tissue, comprising a foreign DNA operably linked to a promoter and encoding said protein, comprising the steps of:

providing cells of a tissue of interest, wherein at least a subset of said cells comprise a foreign DNA sequence operably linked to a promoter and encoding a protein, wherein said cells of said tissue of interest are mixed with an extracellular matrix to create a suspension;

placing said suspension in a vessel having first and second tissue attachment surfaces thereon, wherein the tissue attachment surfaces are positioned such that as the tissue forms in vitro from said cells of said tissue of interest, said cells of said tissue of interest may adhere to said first and second attachment surfaces and align between said attachment surfaces and;

allowing the suspension to coalesce; and culturing said coalesced suspension under conditions in which said organized tissue forms such that said cells form an organized tissue approximating the in vivo gross morphology of said tissue of interest and wherein the organized tissue forms such that a first end and a second end adheres to said tissue attachment surfaces, and wherein tension is maintained between the first and second ends of said organized tissue such that upon detachment of said tissue from one of the tissue attachment surfaces said tissue undergoes a contraction; and implanting said organized tissue into a mammal of the same species as said cells under conditions in which said protein encoded by said foreign DNA is produced.

10. The method of claim 8 or 9, wherein the step of providing comprises isolating primary cells of a cell type of said tissue of interest.

11. The method of claim 8 or 9, wherein the step of providing comprises providing immortalized cells of a cell type of said tissue of interest.

12. The method of claim 8 or 9, wherein said coalesced suspension exerts a force on said cells parallel to a dimension of said vessel.

13. The method of claim 8 or 9, wherein said cells are aligned parallel to a dimension of said vessel.

14. The method of claim 8 or 9, wherein said cells comprise skeletal muscle cells.

15. The method of claim 9, wherein said attachment surfaces are positioned at opposite ends of said vessel.

* * * * *